(12) United States Patent
Mitsuda et al.

(10) Patent No.: US 11,179,307 B2
(45) Date of Patent: Nov. 23, 2021

(54) FOAMABLE COMPOSITION

(71) Applicant: L'OREAL, Paris (FR)

(72) Inventors: Shinobu Mitsuda, Kawasaki (JP); Kazuhiko Maruyama, Kawasaki (JP)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/468,873

(22) PCT Filed: Nov. 24, 2017

(86) PCT No.: PCT/JP2017/043221
§ 371 (c)(1),
(2) Date: Jun. 12, 2019

(87) PCT Pub. No.: WO2018/110311
PCT Pub. Date: Jun. 21, 2018

(65) Prior Publication Data
US 2020/0078283 A1 Mar. 12, 2020

(30) Foreign Application Priority Data
Dec. 15, 2016 (JP) .............................. JP2016-243052

(51) Int. Cl.
| | |
|---|---|
| *A61K 8/81* | (2006.01) |
| *A61K 8/86* | (2006.01) |
| *A61K 8/87* | (2006.01) |
| *A61K 8/04* | (2006.01) |
| *A61K 8/44* | (2006.01) |
| *A61Q 5/00* | (2006.01) |
| *A61Q 19/00* | (2006.01) |

(52) U.S. Cl.
CPC ................ *A61K 8/44* (2013.01); *A61K 8/046* (2013.01); *A61K 8/8147* (2013.01); *A61K 8/86* (2013.01); *A61K 8/87* (2013.01); *A61Q 5/00* (2013.01); *A61Q 19/00* (2013.01); *A61K 2800/48* (2013.01); *A61K 2800/596* (2013.01)

(58) Field of Classification Search
None
See application file for complete search history.

(56) References Cited

U.S. PATENT DOCUMENTS

| | | |
|---|---|---|
| 2007/0161524 A1 | 7/2007 | Counradi et al. |
| 2012/0183492 A1* | 7/2012 | Tominaga .............. A61Q 19/00 424/78.03 |
| 2016/0101040 A1 | 4/2016 | D'Arras |

FOREIGN PATENT DOCUMENTS

| | | | |
|---|---|---|---|
| CN | 103479529 A | 1/2014 | |
| CN | 103479532 A | 1/2014 | |
| CN | 103705428 A | 4/2014 | |
| CN | 106456516 A | 2/2017 | |
| JP | 2002-293722 A | 10/2002 | |
| JP | 2004-161705 A | 6/2004 | |
| JP | 2011-006372 A | 1/2011 | |
| JP | 2014-185125 A | 10/2014 | |
| JP | 2015-074621 A | 4/2015 | |
| JP | 2016-030722 A | 3/2016 | |
| WO | 2011/130460 A1 | 10/2011 | |
| WO | WO2011130460 | * | 10/2011 |
| WO | WO2014195202 | * | 12/2014 |
| WO | WO2015181789 | * | 12/2015 |

OTHER PUBLICATIONS

Ajinomoto, Amino Acid Based Ingredients for Personal Care, Formulation Guide, 2014 (Year: 2014).*
Database GNPD [Online], MINTEL; Jul. 1, 2016 (Jul. 1, 2016), Algenist: "Ultimate Anti-Aging Foaming Cleanser", XP002778438, Database accession No. 4139297 (5 pages).
Database GNPD [Online], MINTEL; Dec. 1, 2012 (Dec. 1, 2012), Ham Products: "Skin Enlightening Cleanser", XP002778439, Database accession No. 1946875 (4 pages).
Database GNPD [Online], MINTEL; Nov. 1, 2015 (Nov. 1, 2015), Meiyue Cosmetic: "Fair Cleansing Mousse", XP002778440, Database accession No. 3581411 (4 pages).
Database GNPD [Online], MINTEL; Mar. 1, 2016 (Mar. 1, 2016), Kao: "Sebum Care Foaming Wash", XP002778441, Database accession No. 3847543 (3 pages).
Database GNPD [Online], MINTEL; Dec. 1, 2009 (Dec. 1, 2009), B&C Laboratories: "Prize Charge Cream", XP002778442, Database accession No. 1221578 (6 pages).
Database GNPD [Online], MINTEL; May 1, 2016 (May 1, 2016), Able C&C: "Whipping Egg Mousse Pack", XP002778443, Database accession No. 4007143 (3 pages).
Database GNPD [Online], MINTEL; Feb. 1, 2016 (Feb. 1, 2016), Lucenbase Bio-Tech: "Moisturizing Cleansing Dream", XP002778444, Database accession No. 3792233 (4 pages).
Database GNPD [Online], MINTEL; Sep. 1, 2011 (Sep. 1, 2011), Kose Cosmeport: "Hyaluronic Acid Cleansing Dream", XP002778445, Database accession No. 1636809 (2 pages).
Database GNPD [Online], MINTEL; Jun. 1, 2011 (Jun. 1, 2011), Mikimoto: "Treatment Essence", XP002778446, Database accession No. 1575753 (4 pages).
Database GNPD [Online], MINTEL; Feb. 1, 2015 (Feb. 1, 2015), Mikimoto Cosmetics: "Recover Essence", XP002778447, Database accession No. 2999111 (6 pages).
Database GNPD [Online], MINTEL; Mar. 1, 2011 (Mar. 1, 2011), Hangzhou Lejin: "Transparent Cleansing Mousse", XP002778448, Database accession No. 1525441 (5 pages).
Database GNPD [Online], MINTEL; Apr. 1, 2012 (Apr. 1, 2012), ICIM International: "Rebalancing Cleansing Water", XP002778449, Database accession No. 1778322 (3 pages).

(Continued)

*Primary Examiner* — Jennifer A Berrios
(74) *Attorney, Agent, or Firm* — Lucas & Mercanti, LLP

(57) ABSTRACT

One embodiment of the present invention relates to a composition comprising: (a) at least one first anionic surfactant selected from glutamic acid compounds and salts thereof; (b) at least one second anionic surfactant selected from alanine compounds and salts thereof, glycine compounds and salts thereof, and mixtures thereof; (c) at least one nonionic surfactant; and (d) at least one thickener. One embodiment according to the present invention is stable and can form foam with good quality.

7 Claims, 1 Drawing Sheet

(56) References Cited

OTHER PUBLICATIONS

Database GNPD [Online], MINTEL; Jun. 1, 2015 (Jun. 1, 2015), Skin Food: "Mask Cream", XP002778450, Database accession No. 3256137 (6 pages).
Database GNPD [Online], MINTEL; Jun. 1, 2015 (Jun. 1, 2015), L'Oreal: "Densifying Mousse", XP002778451, Database accession No. 3261199 (4 pages).
Database GNPD [Online], MINTEL; Apr. 1, 2014 (Apr. 1, 2014), Idelle Labs: "Leave-In Treatment Foaming Mousse", XP002778452, Database accession No. 2367348 (3 pages).
ISA/EP, PCT International Search Report dated Mar. 6, 2018, which was issued in connection with corresponding PCT Application No. PCT/JP2017/043221 (5 pages).
KIPO, Office Action for the corresponding Koran patent application No. 10-2019-7015428, dated Oct. 7, 2020, with English translation.
KIPO, Office Action for the corresponding Korean patent application No. 10-2019-7015428, dated Oct. 7, 2020, with English translation.
JPO, Office Action for the corresponding Japanese patent application No. 2016-243052, dated Nov. 30, 2020, with English translation.
JPO, Notification of Third Party Observation for the corresponding Japanese patent application No. 2016-243052, dated Oct. 19, 2020, with partial English translation.
CNIPA, Office Action for the corresponding Chinese patent application No. 201780074558.6, dated Jul. 1, 2021, with English translation.

\* cited by examiner

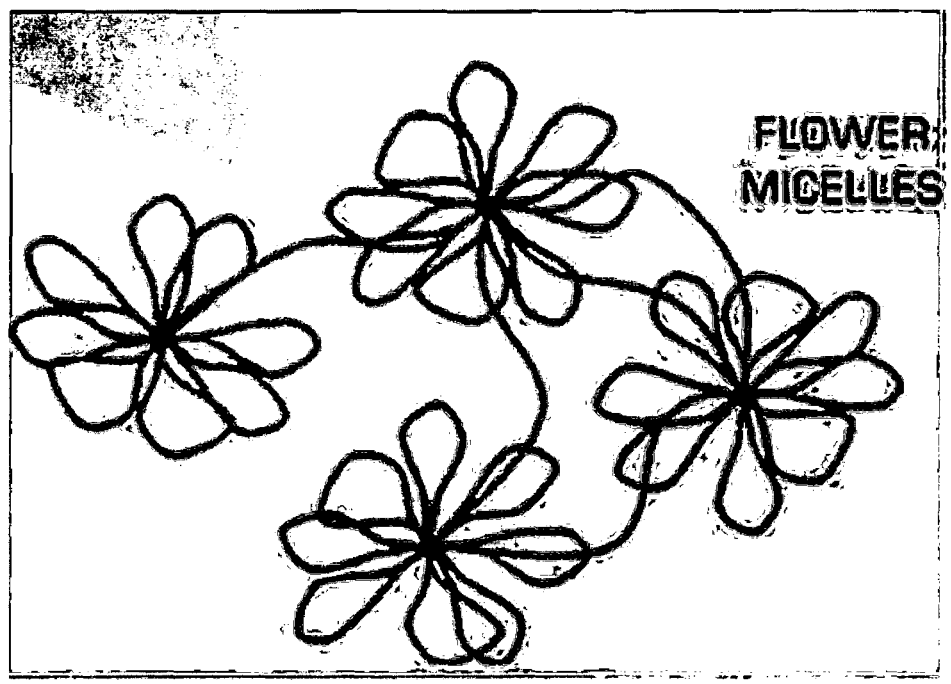

FOAMABLE COMPOSITION

CROSS-REFERENCE TO RELATED APPLICATIONS

This application is a 371 of PCT/JP2017/043221, filed on Nov. 24, 2017, which claims benefit of Japanese Patent Application No. 2016-243052 filed on Dec. 15, 2016, each of which is hereby incorporated by reference in its entirety.

TECHNICAL FIELD

The present invention relates to a composition, preferably a cosmetic or dermatological composition, which includes a specific surfactant system, and therefore is foamable.

BACKGROUND ART

There are several types of foamable cosmetic or dermatological products on the market. One type of such foamable products is a so-called auto-pump product in which a foamable composition is contained in a container with a dispenser which can mix air with the composition to form foam when the composition is discharged from the outlet of the dispenser. The auto-pump products which do not contain gas are more eco-friendly than so-called aerosol type products using a propellant gas, and their transportation is easier than the aerosol type products.

It is preferable that the foamable composition is stable and can form foam with good quality, for example: the foam has fine cells, the foam can provide a sparkling sensation when the foam breaks, and the foam can last for a long period of time.

A foam with fine cells can provide a user with comfort fluffy sensation, as well as fresh sensation when the foam transforms into a liquid. Sparkling sensation can provide a user with feelings of penetration and circulation. Lasting of the foam is necessary for easy application by preventing dripping down during application.

However, conventional foamable compositions lack either sufficient stability or sufficient quality of foam.

Therefore, there is a need for a foamable composition which is stable and can form foam with good quality.

DISCLOSURE OF INVENTION

An objective of the present invention is to provide a foamable composition which is stable and can form foam with good quality.

The above objective of the present invention can be achieved by a composition comprising:
(a) at least one first anionic surfactant selected from glutamic acid compounds and salts thereof;
(b) at least one second anionic surfactant selected from alanine compounds and salts thereof, glycine compounds and salts thereof, and mixtures thereof;
(c) at least one nonionic surfactant; and
(d) at least one thickener.

The (a) first anionic surfactant may be selected from acyl glutamic acids and salts thereof.

The amount of the (a) first anionic surfactant(s) in the composition according to the present invention may range from 0.01 to 10% by weight, preferably from 0.05 to 5% by weight, and more preferably from 0.1 to 3% by weight, relative to the total weight of the composition.

The (b) second anionic surfactant may be selected from acyl alanines and salts thereof.

The (b) second anionic surfactant may be selected from acyl glycines and salts thereof.

The amount of the (b) second anionic surfactant(s) in the composition according to the present invention may range from 0.01 to 10% by weight, preferably from 0.015 to 5% by weight, and more preferably from 0.02 to 3% by weight, relative to the total weight of the composition.

The (c) nonionic surfactant may be selected from polyoxyethylenated (1-40 EO) and polyoxypropylenated (1-30 PO) alkyl ($C_{16}$-$C_{30}$) ethers.

The amount of the (c) nonionic surfactant(s) in the composition according to the present invention may range from 0.001 to 20% by weight, preferably from 0.05 to 10% by weight, and more preferably from 0.1 to 5% by weight, relative to the total weight of the composition.

The (d) thickener may be an associative thickener, preferably an associative polymeric thickener, and more preferably an associative polyurethane thickener, or may be a crosslinked acrylic acid homopolymers.

The (d) thickener may be selected from polyurethane/polyethers comprising in their chain at least one polyoxyethylenated hydrophilic block and at least one of hydrophobic blocks containing at least one sequence chosen from aliphatic sequences, cycloaliphatic sequences, and aromatic sequences, preferably polyurethane/polyethers comprising at least two hydrocarbon-based lipophilic chains having from 8 to 30 carbon atoms, separated by a hydrophilic block, and wherein the hydrocarbon-based chains are chosen from pendent chains and chains at the end of the hydrophilic block, and more preferably polyethyleneglycol-240/decyltetradeceth-20/hexamethylene diisocyanate copolymer, and mixtures thereof.

The amount of the (d) thickener(s) in the composition according to the present invention may range from 0.001 to 20% by weight, preferably from 0.005 to 10% by weight, and more preferably from 0.01 to 5% by weight, relative to the total weight of the composition.

The composition according to the present invention may further comprise water.

The composition according to the present invention may further comprise at least one fatty acid.

The composition according to the present invention may be a cosmetic composition, preferably a cosmetic composition for a keratin substance, and more preferably a skin cosmetic composition.

The present invention also relates to a cosmetic process for treating a keratin substance, comprising the step of applying the composition according to the present invention to the keratin substance.

BRIEF DESCRIPTION OF DRAWINGS

FIG. 1 shows a front view of an example of a network formed by an associative polyurethane thickener in water in which the hydrophobic parts of the associative polyurethane thickener connect to form quasi-micelles which are indicated as flower micelles.

BEST MODE FOR CARRYING OUT THE INVENTION

After diligent research, the inventors have discovered that it is possible to provide a foamable composition which is stable and can form foam with good quality.

Thus, one aspect of the present invention is a composition comprising:
(a) at least one first anionic surfactant selected from glutamic acid compounds and salts thereof;
(b) at least one second anionic surfactant selected from alanine compounds and salts thereof, glycine compounds and salts thereof, and mixtures thereof;
(c) at least one nonionic surfactant; and
(d) at least one thickener.

The present invention includes a specific surfactant system, and therefore is foamable or foaming.

The composition according to the present invention is stable for a long period of time, even under changes in the temperature thereof. Also, the composition according to the present invention can form foam with good quality, for example: the foam has fine cells, the foam can provide a sparkling sensation when the foam breaks, and the foam can last for a long period of time.

Hereinafter, the present invention will be explained in a more detailed manner.

[First Anionic Surfactant]

The composition according to the present invention comprises (a) at least one first anionic surfactant selected from glutamic acid compounds and salts thereof. A single type of first anionic surfactant may be used, but two or more different types of first anionic surfactants may be used in combination.

The glutamic acid compounds encompass glutamic acid and derivatives thereof. Therefore, salts of glutamic acid compounds encompass salts of glutamic acid and derivatives thereof.

The glutamic acid compounds and salts thereof can, for example, be chosen from acyl glutamic acids, their salts (glutamates) and their mixtures, preferably from acyl glutamic acids having an acyl group comprising from 10 to 30 carbon atoms, preferably from 12 to 22 carbon atoms, such as, for example, lauroyl glutamic acid, myristoyl glutamic acid, palmitoyl glutamic acid, stearoyl glutamic acid, behenoyl glutamic acid, olivoyl glutamic acid and cocoyl glutamic acid, and salts thereof, for example, their salts with alkali metals such as Na, Li or K, preferably Na or K, alkaline earth metals such as Mg, and TEA(triethanolamine) as well as the ammonium salts thereof.

It may be preferable that the (a) first anionic surfactant be selected from acyl glutamic acids and salts thereof.

As examples of the acyl glutamic acids and salts thereof, mention may be made of lauroyl glutamic acid, cocoyl glutamic acid, sodium stearoyl glutamate, potassium myristoyl glutamate, potassium lauroyl glutamate, sodium cocoyl glutamate, disodium cocoyl glutamate, TEA-cocoyl glutamate, TEA lauroyl glutamate, potassium cocoyl glutamate, sodium olivoyl glutamate and their mixtures.

Such first anionic surfactants are sold under the name Amisoft by Ajinomoto and in particular under the references Amisoft LA, Amisoft CA, Amisoft HS 11 PF, Amisoft MK-11, Amisoft LK-11, Amisoft CK-11, Amisoft CT-12, Amisoft-CT-12S, Amisoft LT-12 or are also sold by Keminova Italiana SRL.

Mention may also be made of a mixture of first anionic surfactants comprising at least one glutamic acid compound and at least one salt of glutamic acid compound(s), two or more glutamic acid compounds, or two or more salts of the glutamic compound(s) such as, for example, a mixture of acyl glutamates, such as disodium cocoyl glutamate (and) sodium cocoyl glutamate, sold under the name of Amisoft CS-22 by Ajinomoto.

Mention may also be made, as glutamates, of disodium hydrogenated tallow glutamate, such as that sold under the reference Amisoft HS-21 by Ajinomoto.

The amount of the (a) first anionic surfactant(s) in the composition according to the present invention may be 0.01% by weight or more, preferably 0.05% by weight or more, and more preferably 0.1% by weight or more, relative to the total weight of the composition.

On the other hand, the amount of the (a) first anionic surfactant(s) in the composition according to the present invention may be 10% by weight or less, preferably 5% by weight or less, and more preferably 3% by weight or less, relative to the total weight of the composition. It may be even more preferable that the amount of the (a) first anionic surfactant(s) in the composition according to the present invention be 2% by weight or less, relative to the total weight of the composition.

The amount of the (a) first anionic surfactant(s) in the composition according to the present invention may range from 0.01 to 10% by weight, preferably from 0.05 to 5% by weight, more preferably from 0.1 to 3% by weight, relative to the total weight of the composition.

[Second Anionic Surfactant]

The composition according to the present invention comprises (b) at least one second anionic surfactant selected from alanine compounds and salts thereof, glycine compounds and salts thereof, and mixtures thereof. A single type of second anionic surfactant may be used, but two or more different types of second anionic surfactants may be used in combination.

The amount of the (b) second anionic surfactant(s) in the composition according to the present invention may be 0.01% by weight or more, preferably 0.015% by weight or more, and more preferably 0.02% by weight or more, relative to the total weight of the composition.

On the other hand, the amount of the (b) second anionic surfactant(s) in the composition according to the present invention may be 10% by weight or less, preferably 5% by weight or less, and more preferably 3% by weight or less, relative to the total weight of the composition. It may be even more preferable that the amount of the (b) second anionic surfactant(s) in the composition according to the present invention be 1% by weight or less, relative to the total weight of the composition.

The amount of the (b) second anionic surfactant(s) in the composition according to the present invention may range from 0.01 to 10% by weight, preferably from 0.015 to 5% by weight, more preferably from 0.02 to 3% by weight, relative to the total weight of the composition.

(Alanine Compound)

The alanine compounds encompass alanine and derivatives thereof. Therefore, salts of alanine compounds encompass salts of alanine and derivatives thereof.

The alanine compounds and salts thereof can, for example, be chosen from acyl alanines, their salts (alaninates) and their mixtures, preferably from acyl alaninates having an acyl group comprising from 10 to 30 carbon atoms, preferably from 12 to 22 carbon atoms, such as, for example, cocoyl-alanine, N-cocoyl-N-methylalanine, lauroyl-alanine, N-lauroyl-N-methylalanine, myristoyl-alanine, N-myristoyl-N-methylalanine, and salts thereof, for example, their salts with alkali metals such as Na, Li or K, preferably Na or K, alkaline earth metals such as Mg, and TEA(triethanolamine), as well as the ammonium salts thereof.

It may be preferable that the (b) second anionic surfactant be selected from acyl alanines and salts thereof.

As examples of the acyl alanines and salts thereof, mention may be made of sodium cocoyl alaninate, TEA-cocoyl alaninate, and their mixtures.

Such compounds are sold under the name Amilite by Ajinomoto and in particular under the references Amilite ACS-12, Amilite ACT-12 and Amilite ACT-12L.

(Glycine Compound)

The glycine compounds encompass glycine and derivatives thereof. Therefore, salts of glycine compounds (glycinates) encompass salts of glycine and derivatives thereof.

It may be preferable that the (b) second anionic surfactant be selected from the following (1) and (2):

(1) Acyl glycinates of formula (I):

in which

R represents an acyl group R'C—O, with R', which represents a saturated or unsaturated, linear or branched, hydrocarbon chain, preferably comprising from 8 to 30 carbon atoms, more preferably from 9 to 22 carbon atoms, even more preferably from 10 to 20 carbon atoms, and better still from 10 to 16 carbon atoms, and X represents a cation chosen, for example, from ions of alkali metals, such as Na, Li or K, preferably Na or K, ions of alkaline earth metals, such as Mg, TEA (triethanolamine), ammonium groups and their mixtures.

The acyl group can be chosen in particular from the lauroyl, myristoyl, behenoyl, palmitoyl, stearoyl, isostearoyl, olivoyl, cocoyl or oleoyl groups and their mixtures.

Preferably, R is a cocoyl group.

(2) Glycinates of following formula (II):

in which $R_1$ represents a saturated or unsaturated, linear or branched, hydrocarbon chain comprising from 8 to 30 carbon atoms, preferably from 9 to 22 carbon atoms, and better still from 10 to 16 carbon atoms;

$R_1$ is advantageously chosen from the lauryl, myristyl, palmityl, stearyl, cetyl, cetearyl or oleyl groups and their mixtures and preferably from the stearyl and oleyl groups; the $R_2$ groups, which are identical or different, represent an $R_3OH$ group, $R_3$ being an alkyl group comprising from 2 to 10 carbon atoms, preferably from 2 to 5 carbon atoms.

Mention may be made, as compound of formula (I), for example, of sodium cocoyl glycinate, such as, for example, Amilite GCS-12K, sold by Ajinomoto, or potassium cocoyl glycinate, such as, for example, Amilite GCK-12 from Ajinomoto.

Mention may also be made, as compounds of formula (II), of dihydroxyethyl oleyl glycinate or dihydroxyethyl stearyl glycinate.

It may be preferable that the (b) second anionic surfactant be selected from acyl glycines and salts thereof, more preferably from the compounds of formula (I), and even more preferably cocoyl glycinates.

[Nonionic Surfactant]

The composition according to the present invention comprises (c) at least one nonionic surfactant. A single type of nonionic surfactant may be used, but two or more different types of nonionic surfactants may be used in combination.

The nonionic surfactants are compounds well known in themselves (see, e.g., in this regard, "Handbook of Surfactants" by M. R. Porter, Blackie & Son publishers (Glasgow and London), 1991, pp. 116-178). Thus, they can, for example, be chosen from alcohols, alpha-diols, alkylphenols and esters of fatty acids, these compounds being ethoxylated, propoxylated or glycerolated and having at least one fatty chain comprising, for example, from 8 to 30 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils of plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives; amine oxides such as ($C_{10}$-$C_{14}$)alkylamine oxides or N—($C_{10}$-$C_{14}$)acylaminopropylmorpholine oxides; silicone surfactants; and mixtures thereof.

The nonionic surfactants may preferably be chosen from monooxyalkylenated, polyoxyalkylenated, monoglycerolated or polyglycerolated nonionic surfactants. The oxyalkylene units are more particularly oxyethylene or oxypropylene units, or a combination thereof and are preferably oxyethylene units.

Examples of monooxyalkylenated or polyoxyalkylenated nonionic surfactants that may be mentioned include:

monooxyalkylenated or polyoxyalkylenated ($C_8$-$C_{24}$)alkylphenols, saturated or unsaturated, linear or branched, monooxyalkylenated or polyoxyalkylenated $C_8$-$C_{30}$ alcohols, saturated or unsaturated, linear or branched, monooxyalkylenated or polyoxyalkylenated $C_8$-$C_{30}$ amides, esters of saturated or unsaturated, linear or branched, $C_8$-$C_{30}$ acids and of polyalkylene glycols, monooxyalkylenated or polyoxyalkylenated esters of saturated or unsaturated, linear or branched, $C_8$-$C_{30}$ acids and of sorbitol, saturated or unsaturated, monooxyalkylenated or polyoxyalkylenated plant oils, condensates of ethylene oxide and/or of propylene oxide, inter alia, alone or as mixtures.

The surfactants preferably contain a number of moles of ethylene oxide and/or of propylene oxide of between 1 and 100 and most preferably between 2 and 50. Advantageously, the nonionic surfactants do not comprise any oxypropylene units.

According to one of the embodiments of the present invention, the polyoxyalkylenated nonionic surfactants are chosen from polyoxyethylenated fatty alcohol (polyethylene glycol ether of fatty alcohol) and polyoxyethylenated fatty ester (polyethylene glycol ester of fatty acid).

Examples of polyoxyethylenated fatty alcohol (or $C_8$-$C_{30}$ alcohols) that may be mentioned include the adducts of ethylene oxide with lauryl alcohol, especially those containing from 9 to 50 oxyethylene units and more particularly those containing from 10 to 12 oxyethylene units (Laureth-10 to Laureth-12, as the CTFA names); the adducts of ethylene oxide with behenyl alcohol, especially those containing from 9 to 50 oxyethylene units (Beheneth-9 to Beheneth-50, as the CTFA names); the adducts of ethylene oxide with cetearyl alcohol (mixture of cetyl alcohol and stearyl alcohol), especially those containing from 10 to 30 oxyethylene units (Ceteareth-10 to Ceteareth-30, as the CTFA names); the adducts of ethylene oxide with cetyl alcohol, especially those containing from 10 to 30 oxyethylene units (Ceteth-10 to Ceteth-30, as the CTFA names); the adducts of ethylene oxide with stearyl alcohol, especially those containing from 10 to 30 oxyethylene units (Steareth-10 to Steareth-30, as the CTFA names); the adducts of ethylene oxide with isostearyl alcohol, especially those containing from 10 to 50 oxyethylene units (Isosteareth-10 to Isosteareth-50, as the CTFA names); and mixtures thereof.

As examples of monoglycerolated or polyglycerolated nonionic surfactants, monoglycerolated or polyglycerolated $C_8$-$C_{40}$ alcohols are preferably used.

In particular, the monoglycerolated or polyglycerolated $C_8$-$C_{40}$ alcohols correspond to the following formula:

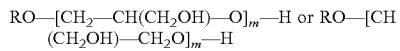

in which R represents a linear or branched $C_8$-$C_{40}$ and preferably $C_8$-$C_{30}$ alkyl or alkenyl radical, and m represents a number ranging from 1 to 30 and preferably from 1.5 to 10.

As examples of compounds that are suitable in the context of the present invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohol may coexist in the form of a mixture.

Among the monoglycerolated or polyglycerolated alcohols, it is preferable to use the $C_8$/$C_{10}$ alcohol containing 1 mol of glycerol, the $C_{10}$/$C_{12}$ alcohol containing 1 mol of glycerol and the $C_{12}$ alcohol containing 1.5 mol of glycerol.

Examples of polyoxyethylenated fatty esters that may be mentioned include the adducts of ethylene oxide with esters of lauric acid, palmitic acid, stearic acid or behenic acid, and mixtures thereof, especially those containing from 9 to 100 oxyethylene units, such as PEG-9 to PEG-50 laurate (CTFA names: PEG-9 laurate to PEG-50 laurate); PEG-9 to PEG-50 palmitate (CTFA names: PEG-9 palmitate to PEG-50 palmitate); PEG-9 to PEG-50 stearate (CTFA names: PEG-9 stearate to PEG-50 stearate); PEG-9 to PEG-50 palmitostearate; PEG-9 to PEG-50 behenate (CTFA names: PEG-9 behenate to PEG-50 behenate); polyethylene glycol 100 EO monostearate (CTFA name: PEG-100 stearate); and mixtures thereof.

According to one of the embodiments of the present invention, the nonionic surfactant may be selected from esters of polyols with fatty acids with a saturated or unsaturated chain containing for example from 8 to 24 carbon atoms, preferably 12 to 22 carbon atoms, and polyoxyalkylenated derivatives thereof, preferably containing from 10 to 200, and more preferably from 10 to 100 oxyalkylene units, such as glyceryl esters of a $C_8$-$C_{24}$, preferably $C_{12}$-$C_{22}$, fatty acid or acids and polyoxyalkylenated derivatives thereof, preferably containing from 10 to 200, and more preferably from 10 to 100 oxyalkylene units; sorbitol esters of a $C_8$-$C_{24}$, preferably $C_{12}$-$C_{22}$, fatty acid or acids and polyoxyalkylenated derivatives thereof, preferably containing from 10 to 200, and more preferably from 10 to 100 oxyalkylene units; sugar (sucrose, maltose, glucose, fructose, and/or alkylglycose) esters of a $C_8$-$C_{24}$, preferably $C_{12}$-$C_{22}$, fatty acid or acids and polyoxyalkylenated derivatives thereof, preferably containing from 10 to 200, and more preferably from 10 to 100 oxyalkylene units; ethers of fatty alcohols; ethers of sugar and a $C_8$-$C_{24}$, preferably $C_{12}$-$C_{22}$, fatty alcohol or alcohols; and mixtures thereof.

As glyceryl esters of fatty acids, glyceryl stearate (glyceryl mono-, di- and/or tristearate) (CTFA name: glyceryl stearate) or glyceryl ricinoleate and mixtures thereof can be cited, and as polyoxyalkylenated derivatives thereof, mono-, di- or triester of fatty acids with a polyoxyalkylenated glycerol (mono-, di- or triester of fatty acids with a polyalkylene glycol ether of glycerol), preferably polyoxyethylenated glyceryl stearate (mono-, di- and/or tristearate), such as PEG-20 glyceryl stearate (mono-, di- and/or tristearate) can be cited.

Mixtures of these surfactants, such as, for example, the product containing glyceryl stearate and PEG-100 stearate, marketed under the name ARLACEL 165 by Uniqema, and the product containing glyceryl stearate (glyceryl mono- and distearate) and potassium stearate marketed under the name TEGIN by Goldschmidt (CTFA name: glyceryl stearate SE), can also be used.

The sorbitol esters of $C_8$-$C_{24}$ fatty acids and polyoxyalkylenated derivatives thereof can be selected from sorbitan palmitate, sorbitan isostearate, sorbitan trioleate and esters of fatty acids and alkoxylated sorbitan containing for example from 20 to 100 EO, such as, for example, sorbitan monostearate (CTFA name: sorbitan stearate), sold by the company ICI under the name Span 60, sorbitan monopalmitate (CTFA name: sorbitan palmitate), sold by the company ICI under the name Span 40, and sorbitan tristearate 20 EO (CTFA name: polysorbate 65), sold by the company ICI under the name Tween 65, polyethylene sorbitan trioleate (polysorbate 85) or the compounds marketed under the trade names Tween 20 or Tween 60 by Uniqema.

As esters of fatty acids and glucose or alkylglucose, glucose palmitate, alkylglucose sesquistearates such as methylglucose sesquistearate, alkylglucose palmitates such as methylglucose or ethylglucose palmitate, methylglucoside fatty esters, the diester of methylglucoside and oleic acid (CTFA name: Methyl glucose dioleate), the mixed ester of methylglucoside and the mixture of oleic acid/hydroxystearic acid (CTFA name: Methyl glucose dioleate/hydroxystearate), the ester of methylglucoside and isostearic acid (CTFA name: Methyl glucose isostearate), the ester of methylglucoside and lauric acid (CTFA name: Methyl glucose laurate), the mixture of monoester and diester of methylglucoside and isostearic acid (CTFA name: Methyl glucose sesqui-isostearate), the mixture of monoester and diester of methylglucoside and stearic acid (CTFA name: Methyl glucose sesquistearate) and in particular the product marketed under the name Glucate SS by AMERCHOL, and mixtures thereof can be cited.

As ethoxylated ethers of fatty acids and glucose or alkylglucose, ethoxylated ethers of fatty acids and methylglucose, and in particular the polyethylene glycol ether of the diester of methylglucose and stearic acid with about 20 moles of ethylene oxide (CTFA name: PEG-20 methyl glucose distearate) such as the product marketed under the name Glucam E-20 distearate by AMERCHOL, the polyethylene glycol ether of the mixture of monoester and diester of methyl-glucose and stearic acid with about 20 moles of ethylene oxide (CTFA name: PEG-20 methyl glucose sesquistearate) and in particular the product marketed under the name Glucamate SSE-20 by AMERCHOL and that marketed under the name Grillocose PSE-20 by GOLDSCHMIDT, and mixtures thereof, can for example be cited.

As sucrose esters, saccharose palmito-stearate, saccharose stearate and saccharose monolaurate can for example be cited.

As sugar ethers, alkylpolyglucosides can be used, and for example decylglucoside such as the product marketed under the name MYDOL 10 by Kao Chemicals, the product marketed under the name PLANTAREN 2000 by Henkel, and the product marketed under the name ORAMIX NS 10 by Seppic, caprylyl/capryl glucoside such as the product marketed under the name ORAMIX CG 110 by Seppic or under the name LUTENSOL GD 70 by BASF, laurylglucoside such as the products marketed under the names PLANTAREN 1200 N and PLANTACARE 1200 by Henkel, coco-glucoside such as the product marketed under the name PLANTACARE 818/UP by Henkel, cetostearyl glucoside possibly mixed with cetostearyl alcohol, marketed for example under the name MONTANOV 68 by Seppic, under the name TEGO-CARE CG90 by Goldschmidt and under the name EMULGADE KE3302 by Henkel, arachidyl glucoside, for example in the form of the mixture of arachidyl and behenyl alcohols and arachidyl glucoside marketed under the name MONTANOV 202 by Seppic, cocoylethylglucoside, for example in the form of the mixture (35/65) with cetyl and stearyl alcohols, marketed under the name MONTANOV 82 by Seppic, and mixtures thereof can in particular be cited.

Mixtures of glycerides of alkoxylated plant oils such as mixtures of ethoxylated (200 EO) palm and copra (7 EO) glycerides can also be cited.

The nonionic surfactant according to the present invention preferably contains alkenyl or branched $C_{12}$-$C_{22}$ acyl chain such as oleyl or isostearyl group. More preferably, the nonionic surfactant according to the present invention is PEG-20 glyceryl triisostearate.

According to one of the embodiments of the present invention, the nonionic surfactant may be selected from polyoxyethylenated (1-40 EO) and polyoxypropylenated (1-30 PO) alkyl ($C_{16}$-$C_{30}$) ethers.

The polyoxyethylenated (1-40 EO) and polyoxypropylenated (1-30 PO) alkyl ($C_{16}$-$C_{30}$) ethers which may be used as surfactants in the nanoemulsion according to the present invention, may be selected from the group consisting of:
PPG-6 Decyltetradeceth-30; Polyoxyethlene (30) Polyoxypropylene (6) Tetradecyl Ether such as those sold as Nikkol PEN-4630 from Nikko Chemicals Co.,
PPG-6 Decyltetradeceth-12; Polyoxyethylene (12) Polyoxypropylene (6) Tetradecyl Ether such as those sold as Nikkol PEN-4612 from Nikko Chemicals Co.,
PPG-13 Decyltetradeceth-24; Polyoxyethylene (24) Polyoxypropylene (13) Decyltetradecyl Ether such as those sold as UNILUBE 50MT-2200B from NOF Corporation,
PPG-6 Decyltetradeceth-20; Polyoxyethylene (20) Polyoxypropylene (6) Decyltetradecyl Ether such as those sold as Nikkol PEN-4620 from Nikko Chemicals Co.,
PPG-4 Ceteth-1; Polyoxyethylene (1) Polyoxypropylene (4) Cetyl Ether such as those sold as Nikkol PBC-31 from Nikko Chemicals Co.,
PPG-8 Ceteth-1; Polyoxyethylene (1) Polyoxypropylene (8) Cetyl Ether such as those sold as Nikkol PBC-41 from Nikko Chemicals Co.,
PPG-4 Ceteth-10; Polyoxyethylene (10) Polyoxypropylene (4) Cetyl Ether such as those sold as Nikkol PBC-33 from Nikko Chemicals Co.,
PPG-4 Ceteth-20; Polyoxyethylene (20) Polyoxypropylene (4) Cetyl Ether such as those sold as Nikkol PBC-34 from Nikko Chemicals Co.,
PPG-5 Ceteth-20; Polyoxyethylene (20) Polyoxypropylene (5) Cetyl Ether such as those sold as Procetyl AWS from Croda Inc.,
PPG-8 Ceteth-20; Polyoxyethylene (20) Polyoxypropylene (8) Cetyl Ether such as those sold as Nikkol PBC-44 from Nikko Chemicals Co., and
PPG-23 Steareth-34; Polyoxyethylene Polyoxypropylene Stearyl Ether (34 EO) (23 PO) such as those sold as Unisafe 34S-23 from Pola Chemical Industries.

It is more preferable that the polyoxyethylenated (1-40 EO) and polyoxypropylenated (1-30 PO) alkyl ($C_{16}$-$C_{30}$) ethers are (15-40 EO) and polyoxypropylenated (5-30 PO) alkyl ($C_{16}$-$C_{24}$) ethers, which could be selected from the group consisting of PPG-6 Decyltetradeceth-30, PPG-13 Decyltetradeceth-24, PPG-6 Decyltetradeceth-20, PPG-5 Ceteth-20, PPG-8 Ceteth-20, and PPG-23 Steareth-34.

It is most preferable that the polyoxyethylenated (1-40 EO) and polyoxypropylenated (1-30 PO) alkyl ($C_{16}$-$C_{30}$) ethers are (15-40 EO) and polyoxypropylenated (5-30 PO) alkyl ($C_{16}$-$C_{24}$) ethers, which could be selected from the group consisting of PPG-6 Decyltetradeceth-30, PPG-13 Decyltetradeceth-24, PPG-5 Ceteth-20, and PPG-8 Ceteth-20. They can also provide a composition with transparency for a long time.

According to one of the embodiments of the present invention, the nonionic surfactant may be selected from copolymers of ethylene oxide and of propylene oxide, in particular copolymers of the following formula:

$$HO(C_2H_4O)_a(C_3H_6O)_b(C_2H_4O)_cH$$

in which a, b and c are integers such that a+c ranges from 2 to 100 and b ranges from 14 to 60, and mixtures thereof.

The nonionic surfactant may be selected from silicone surfactants. Non-limiting mention may be made of those disclosed in documents U.S. Pat. Nos. 5,364,633 and 5,411,744.

The silicone surfactant may preferably be a compound of formula (I):

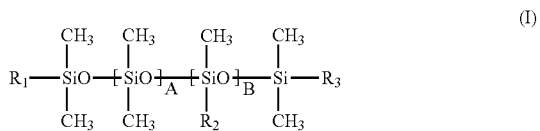

in which:
$R_1$, $R_2$ and $R_3$, independently of each other, represent a $C_1$-$C_6$ alkyl radical or a radical —$(CH_2)_x$—$(OCH_2CH_2)_y$—$(OCH_2CH_2CH_2)_z$—$OR_4$, at least one radical $R_1$, $R_2$ or $R_3$ not being an alkyl radical; $R_4$ being a hydrogen, an alkyl radical or an acyl radical;
A is an integer ranging from 0 to 200;
B is an integer ranging from 0 to 50; with the proviso that A and B are not simultaneously equal to zero;
x is an integer ranging from 1 to 6;
y is an integer ranging from 1 to 30;
z is an integer ranging from 0 to 5.

According to one preferred embodiment of the present invention, in the compound of formula (I), the alkyl radical is a methyl radical, x is an integer ranging from 2 to 6 and y is an integer ranging from 4 to 30.

As examples of silicone surfactants of formula (I), mention may be made of the compounds of formula (II):

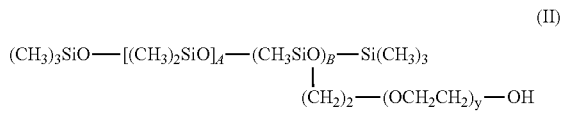

in which A is an integer ranging from 20 to 105, B is an integer ranging from 2 to 10 and y is an integer ranging from 10 to 20.

As examples of silicone surfactants of formula (I), mention may also be made of the compounds of formula (III):

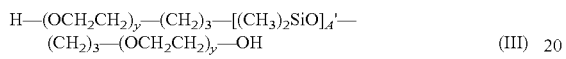

in which A' and y are integers ranging from 10 to 20.

Compounds of the present invention which may be used are those sold by the company Dow Corning under the names DC 5329, DC 7439-146, DC 2-5695 and Q4-3667. The compounds DC 5329, DC 7439-146 and DC 2-5695 are compounds of formula (II) in which, respectively, A is 22, B is 2 and y is 12; A is 103, B is 10 and y is 12; A is 27, B is 3 and y is 12.

The compound Q4-3667 is a compound of formula (III) in which A is 15 and y is 13.

It may be preferable that (c) nonionic surfactant be selected from polyoxyethylenated (1-40 EO) and polyoxypropylenated (1-30 PO) alkyl ($C_{16}$-$C_{30}$) ethers as explained above.

The amount of the (c) nonionic surfactant(s) in the composition according to the present invention may be 0.001% by weight or more, preferably 0.005% by weight or more, and more preferably 0.01% by weight or more, relative to the total weight of the composition. It may be even more preferable that the amount of the (c) nonionic surfactant(s) in the composition according to the present invention be 0.1% by weight or more, relative to the total weight of the composition.

On the other hand, the amount of the (c) nonionic surfactant(s) in the composition according to the present invention may be 20% by weight or less, preferably 10% by weight or less, and more preferably 5% by weight or less, relative to the total weight of the composition. It may be even more preferable that the amount of the (c) nonionic surfactant(s) in the composition according to the present invention be 1% by weight or less, relative to the total weight of the composition.

The amount of the (c) nonionic surfactant(s) in the composition according to the present invention may range from 0.001 to 20% by weight, preferably from 0.005 to 10% by weight, more preferably from 0.01 to 5% by weight, relative to the total weight of the composition. It may be even more preferable that the amount of the (c) nonionic surfactant(s) in the composition according to the present invention be from 0.1% to 1% by weight, relative to the total weight of the composition.

[Thickener]

The composition according to the present invention comprises (d) at least one thickener. A single type of thickener may be used, but two or more different types of thickeners may be used in combination.

It is preferable that the (d) thickener be selected from the group consisting of:
(i) associative thickeners;
(ii) crosslinked acrylic acid homopolymers;
(iii) crosslinked copolymers of (meth)acrylic acid and of ($C_1$-$C_6$)alkyl acrylate;
(iv) nonionic homopolymers and copolymers comprising ethylenically unsaturated monomers of ester and/or amide type;
(v) ammonium acrylate homopolymers and copolymers of ammonium acrylate and of acrylamide;
(vi) polysaccharides; and
(vii) $C_{12}$-$C_{30}$ fatty alcohols.

It is preferable that the (d) thickener is selected from associative thickeners.

(i) As used herein, the expression "associative thickener" means an amphiphilic thickener comprising both hydrophilic units and hydrophobic units, for example, at least one $C_8$-$C_{30}$ fatty chain and at least one hydrophilic unit.

Representative associative thickeners that may be used are associative polymers chosen from:
(aa) nonionic amphiphilic polymers comprising at least one fatty chain and at least one hydrophilic unit;
(bb) anionic amphiphilic polymers comprising at least one hydrophilic unit and at least one fatty-chain unit;
(cc) cationic amphiphilic polymers comprising at least one hydrophilic unit and at least one fatty-chain unit; and
(dd) amphoteric amphiphilic polymers comprising at least one hydrophilic unit and at least one fatty-chain unit, wherein the fatty chain contains from 10 to 30 carbon atoms.

The (aa) nonionic amphiphilic polymers comprising at least one fatty chain and at least one hydrophilic unit may, for example, be chosen from:
(1) celluloses modified with groups comprising at least one fatty chain; examples that may be mentioned include:
hydroxyethylcelluloses modified with groups comprising at least one fatty chain chosen from alkyl, arylalkyl, and alkylaryl groups, and in which the alkyl groups are, for example, $C_8$-$C_{22}$, such as the product Natrosol Plus Grade 330 CS($C_{1-6}$ alkyls) sold by the company Aqualon, and the product Bermocoll EHM 100 sold by the company Berol Nobel, and
celluloses modified with polyalkylene glycol alkylphenyl ether groups, such as the product Amercell Polymer HM-1500 (polyethylene glycol (15) nonylphenyl ether) sold by the company Amerchol.
(2) hydroxypropyl guars modified with groups comprising at least one fatty chain, such as the product Esaflor HM 22 ($C_{22}$ alkyl chain) sold by the company Lamberti, and the products Miracare XC95-3 ($C_{14}$ alkyl chain) and RE205-1 ($C_{20}$ alkyl chain) sold by the company Rhodia Chimie.
(3) polyether urethanes comprising at least one fatty chain, such as $C_{10}$-$C_{30}$ alkyl or alkenyl groups, for instance the products Elfacos T 210 and Elfacos T 212 sold by the company Akzo or the products Aculyn 44 and Aculyn 46 sold by the company Rohm & Haas.
(4) copolymers of vinylpyrrolidone and of hydrophobic fatty-chain monomers; examples that may be mentioned include:
the products Antaron V216 and Ganex V216 (vinylpyrrolidone/hexadecene copolymer) sold by the company I.S.P., and
the products Antaron V220 and Ganex V220 (vinylpyrrolidone/eicosene copolymer) sold by the company I.S.P.

(5) copolymers of $C_1$-$C_6$ alkyl acrylates or methacrylates and of amphiphilic monomers comprising at least one fatty chain, such as the oxyethylenated methyl methacrylate/stearyl acrylate copolymer sold by the company Goldschmidt under the name Antil 208.

(6) copolymers of hydrophilic acrylates or methacrylates and of hydrophobic monomers comprising at least one fatty chain, such as a polyethylene glycol methacrylate/lauryl methacrylate copolymer.

The (bb) anionic amphiphilic polymers comprising at least one hydrophilic unit and at least one fatty-chain unit, may, for example, be chosen from those comprising at least one fatty-chain allyl ether unit and at least one hydrophilic unit comprising an ethylenic unsaturated anionic monomeric unit, for example, a vinylcarboxylic acid unit and further, for example, be chosen from units derived from acrylic acids, methacrylic acids, and mixtures thereof, wherein the fatty-chain allyl ether unit corresponds to the monomer of formula (I) below:

$$CH_2=C(R_1)CH_2OB_nR \qquad (I)$$

in which $R_1$ is chosen from H and $CH_3$, B is an ethyleneoxy radical, n is chosen from zero and integers ranging from 1 to 100, R is chosen from hydrocarbon-based radicals chosen from alkyl, arylalkyl, aryl, alkylaryl, and cycloalkyl radicals, containing from 10 to 30 carbon atoms, and further, for example, from 10 to 24 carbon atoms and even further, for example, from 12 to 18 carbon atoms.

In one embodiment, a unit of formula (I) is, for example, a unit in which $R_1$ can be H, n can be equal to 10, and R can be a stearyl ($C_{18}$) radical.

Anionic amphiphilic polymers of this type are described and prepared, according to an emulsion polymerization process, in patent EP-0 216 479 B2.

In one embodiment, anionic amphiphilic polymers are, for example, polymers formed from 20% to 60% by weight of acrylic acid and/or of methacrylic acid, from 5% to 60% by weight of lower alkyl (meth)acrylates, from 2% to 50% by weight of fatty-chain allyl ether of formula (I), and from 0% to 1% by weight of a crosslinking agent which is a well-known copolymerizable unsaturated polyethylenic monomer, for example, diallyl phthalate, allyl(meth)acrylate, divinylbenzene, (poly)ethylene glycol dimethacrylate, and methylenebisacrylamide.

Examples of such polymers are crosslinked terpolymers of methacrylic acid, of ethyl acrylate, and of polyethylene glycol (10 EO) stearyl ether (Steareth-10), such as those sold by the company Ciba under the names Salcare SC 80 and Salcare SC 90, which are aqueous 30% emulsions of a crosslinked terpolymer of methacrylic acid, of ethyl acrylate, and of steareth-10 allyl ether (40/50/10).

The anionic amphiphilic polymers may further be chosen, for example, from those comprising at least one hydrophilic unit of unsaturated olefinic carboxylic acid type, and at least one hydrophobic unit of a type such as a ($C_{10}$-$C_{30}$) alkyl ester of an unsaturated carboxylic acid. The hydrophilic unit of unsaturated olefinic carboxylic acid type corresponds to, for example, the monomer of formula (II) below:

(II)

in which $R^1$ is chosen from H, $CH_3$, and $C_2H_5$, i.e., acrylic acid, methacrylic acid, and ethacrylic acid units. The hydrophobic unit of a type such as a ($C_{10}$-$C_{30}$) alkyl ester of an unsaturated carboxylic acid corresponds to, for example, the monomer of formula (III) below:

(III)

in which $R^1$ is chosen from H, $CH_3$, and $C_2H_5$ (i.e., acrylate, methacrylate, and ethacrylate units) and is, for example, chosen from, for example, H (acrylate units) and $CH_3$ (methacrylate units), and $R^2$ is chosen from $C_{10}$-$C_{30}$ alkyl radicals, for example, $C_{12}$-$C_{22}$ alkyl radicals.

Examples of ($C_{10}$-$C_{30}$)alkyl esters of unsaturated carboxylic acids include lauryl acrylate, stearyl acrylate, decyl acrylate, isodecyl acrylate, and dodecyl acrylate, and the corresponding methacrylates, lauryl methacrylate, stearyl methacrylate, decyl methacrylate, isodecyl methacrylate, and dodecyl methacrylate.

Anionic amphiphilic polymers of this type are disclosed and prepared, for example, according to U.S. Pat. Nos. 3,915,921 and 4,509,949.

Representative anionic amphiphilic polymers that can be used may further be chosen from polymers formed from a mixture of monomers comprising:

(7) acrylic acid, an ester of formula (IV) below:

(IV)

in which $R^1$ is chosen from H and $CH_3$, $R^2$ is chosen from $C_{10}$-$C_{30}$ alkyl radicals, such as alkyl radicals containing from 12 to 22 carbon atoms, and a crosslinking agent; such as polymers derived from 95% to 60% by weight of the acrylic acid (hydrophilic unit), 4% to 40% by weight of $C_{10}$-$C_{30}$ alkyl acrylate (hydrophobic unit), and 0% to 6% by weight of crosslinking polymerizable monomer, or polymers derived from 98% to 96% by weight of the acrylic acid (hydrophilic unit), 1% to 4% by weight of $C_{10}$-$C_{30}$ alkyl acrylate (hydrophobic unit), and 0.1% to 0.6% by weight of crosslinking polymerizable monomer; or (8) acrylic acid and lauryl methacrylate, such as the polymers formed from 66% by weight of acrylic acid and 34% by weight of lauryl methacrylate.

The crosslinking agent can be a monomer comprising a group

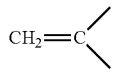

with at least one other polymerizable group whose unsaturated bonds are not conjugated.

Mention may be made, for example, of polyallyl ethers such as polyallylsucrose and polyallylpentaerythritol.

Among said polymers above, mention may be made, for example, of the products sold by the company Goodrich under the trade names Pemulen TR1, Pemulen TR2, and Carbopol 1382, and further, for example, Pemulen TR1, and the product sold by the company S.E.P.C. under the name Coatex SX.

Among anionic amphiphilic fatty-chain polymers, mention may also be made, for example, of the ethoxylated copolymer of methacrylic acid/methyl acrylate/alkyl dimethyl-meta-isopropenylbenzylisocyanate sold under the name Viscophobe DB 1000 by the company Amerchol.

The (cc) cationic amphiphilic polymers used are, for example, chosen from quaternized cellulose derivatives and polyacrylates comprising amino side groups.

The quaternized cellulose derivatives are, for example, chosen from quaternized celluloses modified with groups comprising at least one fatty chain, such as alkyl, arylalkyl, and alkylaryl groups comprising at least 8 carbon atoms, and mixtures thereof, and quaternized hydroxyethylcelluloses modified with groups comprising at least one fatty chain, such as alkyl, arylalkyl, and alkylaryl groups comprising at least 8 carbon atoms, and mixtures thereof.

Quaternized and non-quaternized polyacrylates comprising amino side groups have, for example, hydrophobic groups, such as Steareth 20 (polyoxy-ethylenated(20) stearyl alcohol) and ($C_{10}$-$C_{30}$)alkyl PEG-20 itaconate.

The alkyl radicals borne by the above quaternized celluloses and hydroxyethylcelluloses, for example, contain from 8 to 30 carbon atoms.

The aryl radicals, for example, are chosen from phenyl, benzyl, naphthyl, and anthryl groups.

Examples of quaternized alkylhydroxyethyl-celluloses comprising $C_8$-$C_{30}$ fatty chains are the products Quatrisoft LM 200, Quatrisoft LM-X 529-18-A, Quatrisoft LM-X 529-18B ($C_{12}$ alkyl), and Quatrisoft LM-X 529-8 ($C_{18}$ alkyl) sold by the company Amerchol, and the products Crodacel QM, Crodacel QL ($C_{12}$ alkyl), and Crodacel QS ($C_{18}$ alkyl) sold by the company Croda.

Examples of polyacrylates comprising amino side chains are the polymers 8781-124B or 9492-103 and Structure Plus from the company National Starch.

Among the (dd) amphoteric amphiphilic polymers comprising at least one hydrophilic unit and at least one fatty-chain unit, mention may be made, for example, of copolymers of methacrylamidopropyltrimethylammonium chloride/acrylic acid/$C_{10}$-$C_{30}$ alkyl methacrylate, wherein the alkyl radical is, for example, a stearyl radical.

The associative thickeners in the compositions can have, for example, in solution or in dispersion at a concentration of 1% active material in water, a viscosity, measured using a Rheomat RM 180 rheometer at 25° C., of greater than 0.1 ps and further, for example, of greater than 0.2 cp, at a shear rate of 200 $s^{-1}$.

The associative thickener may be an associative polymeric thickener, preferably an associative polyurethane thickener.

The associative polyurethane thickener may be cationic or nonionic.

Among the associative polyurethane thickeners, there may be mention of the associative polyurethane derivatives such as those obtained by polymerization: about 20% to 70% by weight of a carboxylic acid containing an α,β-monoethylenic unsaturation, about 20 to 80% by weight of a nonsurfactant monomer containing an α,β-monoethylenic unsaturation, about 0.5 to 60% by weight of a nonionic mono-urethane which is the product of the reaction of a monohydroxylated surfactant with a monoethylenically unsaturated monoisocyanate.

The like are described in particular in EP 173109 and more particularly in example 3. More precisely, this polymer is a methacrylic acid/methyl acrylate/dimethyl metaisopropenyl benzyl isocyanate of ethoxylated behenyl alcohol (40EO) terpolymer as an aqueous dispersion at 25%. This product is provided under the reference VISCOPHOBE DB1000 by the company AMERCHOL.

Also suitable are the cationic associative polyurethane thickeners the family of which has been described by the Applicant in French Patent Application No. 0009609. They can be represented more particularly by the following general formula (A): R—X—$(P)_n$-[L-$(Y)_m]_r$-L'-$(P')_p$—X'—R' (A) in which: R and R', which are identical or different, represent a hydrophobic group or a hydrogen atom; X and X', which are identical or different, represent a group containing an amine functional group carrying or otherwise a hydrophobic group, or alternatively the group L"; L, L' and L", which are identical or different, represent a group derived from a diisocyanate; P and P', which are identical or different, represent a group containing an amine functional group carrying or otherwise a hydrophobic group; Y represents a hydrophilic group; r is an integer between 1 and 100, preferably between 1 and 50 and in particular between 1 and 25; n, m and p are each independently of the others between 0 and 1000; the molecule containing at least one protonated or quaternized amine functional group and at least one hydrophobic group.

In a very advantageous embodiment, the only hydrophobic groups of these polyurethanes are the groups R and R' at the chain ends.

According to a first preferred embodiment, the associative polyurethane thickener corresponds to the formula (A) in which R and R' both represent independently a hydrophobic group, X, X' each represent a group L", n and p are between 1 and 1000, and L, L', L", P, P', Y and m have the meaning indicated in formula (A).

According to another preferred embodiment of the present invention, the associative polyurethane thickener corresponds to the formula (A) in which R and R' both represent independently a hydrophobic group, X, X' each represent a group L", n and p are equal to 0, and L, L", Y and m have the meaning in formula (A) indicated above.

The fact that n and p are equal to 0 means that these polymers do not contain units derived from a monomer containing an amine functional group, incorporated into the polymer during polycondensation. The protonated amine functional groups of these polyurethanes result from the hydrolysis of isocyanate functional groups, in excess, at the chain end, followed by alkylation of the primary amine functional groups formed by alkylating agents containing a hydrophobic group, that is to say compounds of the RQ or R'Q type, in which R and R' are as defined above and Q denotes a leaving group such as a halide, a sulfate and the like.

In accordance with another preferred embodiment of the present invention, the associative polyurethane thickener corresponds to formula (A) in which R and R' both represent independently a hydrophobic group, X and X' both represent independently a group containing a quaternary amine, n and p are equal to zero, and L, L', Y and m have the meaning indicated in formula (A).

The number-average molecular mass of the cationic associative polyurethane thickeners is usually between 400 and 500 000, in particular between 1000 and 400 000, and ideally between 1000 and 300 000 g/mol.

When X and/or X' denote a group containing a tertiary or quaternary amine, X and/or X' may represent one of the following formulae:

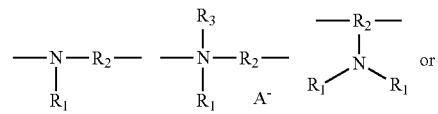

-continued

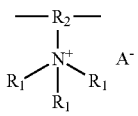

for X

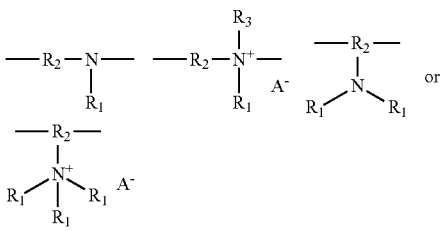

for X' in which:

R$_2$ represents a linear or branched alkylene radical having from 1 to 20 carbon atoms, containing or otherwise a saturated or unsaturated ring, or an arylene radical, it being possible for one or more of the carbon atoms to be replaced by a heteroatom chosen from N, S, O, P;

R$_1$ and R$_3$, which are identical or different, denote a linear or branched, C$_1$-C$_{30}$ alkyl or alkenyl radical, an aryl radical, it being possible for at least one of the carbon atoms to be replaced by a heteroatom chosen from N, S, O, and P;

A' is a physiologically acceptable counterion.

The groups L, L' and L" represent a group of formula:

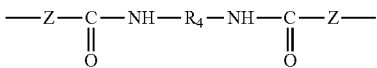

in which:

Z represents —O—, —S— or —NH—; and

R$_4$ represents a linear or branched alkylene radical having from 1 to 20 carbon atoms, containing or otherwise a saturated or unsaturated ring, an arylene radical, it being possible for one or more of the carbon atoms to be replaced by a heteroatom chosen from N, S, O and P.

The groups P and P', comprising an amine functional group, may represent at least one of the following formulae:

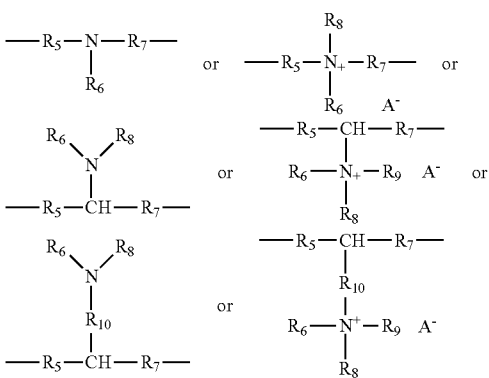

or in which:

R$_5$ and R$_7$ have the same meanings as R$_2$ defined above; R$_6$, R$_8$ and R$_9$ have the same meanings as R$_1$ and R$_3$ defined above;

R$_{10}$ represents a linear or branched alkylene group, which is optionally unsaturated and which may contain one or more heteroatoms chosen from N, O, S and P;

A$^-$ is a physiologically acceptable counterion.

As regards the meaning of Y, the expression hydrophilic group is understood to mean a polymeric or nonpolymeric water-soluble group. By Way of example, there may be mentioned, when polymers are not involved, ethylene glycol, diethylene glycol and propylene glycol. In accordance with a preferred embodiment, in the case of a hydrophilic polymer, there may be mentioned, by way of example, polyethers, sulfonated polyesters, sulfonated polyamides, or a mixture of these polymers. Preferably, the hydrophilic compound is a polyether and in particular a polyethylene oxide or a polypropylene oxide.

The cationic associative polyurethane thickeners of formula (A) are formed from diisocyanates and from various compounds possessing functional groups containing a labile hydrogen. The functional groups containing a labile hydrogen may be alcohol functional groups, primary or secondary amine functional groups or thiol functional groups which give, after reaction with the diisocyanate functional groups, polyurethanes, polyureas and polythioureas, respectively. The term "polyurethanes" of the present invention covers these three types of polymer, namely polyurethanes proper, polyureas and polythioureas and copolymers thereof.

A first type of compounds entering into the preparation of the polyurethane of formula (A) is a compound containing at least one unit containing an amine functional group. This compound may be multifunctional, but preferably the compound is difunctional, that is to say, according to a preferred embodiment, this compound contains two labile hydrogen atoms carried for example by a hydroxyl, primary amine, secondary amine or thiol functional group. It is also possible to use a mixture of multifunctional and difunctional compounds in which the percentage of multifunctional compounds is low.

As indicated above, this compound may contain more than one unit containing an amine functional group. It is then a polymer carrying a repeat of the unit containing an amine functional group.

This type of compound may be represented by one of the following formulae: HZ—(P)$_n$—ZH, or HZ—(P')$_p$—ZH, in which Z, P, P', n and p are as defined above.

By way of examples of a compound containing an amine functional group, there may be mentioned N-methyldiethanolamine, N-tert-butyldiethanolamine, N-sulfoethyldiethanolamine.

The second compound entering into the preparation of the polyurethane of formula (A) is a diisocyanate corresponding to the formula O═C═N—R$_4$—N═C═O in which R$_4$ is defined above.

By way of example, there may be mentioned methylenediphenyl diisocyanate, methylenecyclohexane diisocyanate, isophorone diisocyanate, toluene diisocyanate, naphthalene diisocyanate, butane diisocyanate, and hexane diisocyanate.

A third compound entering into the preparation of the polyurethane of formula (A) is a hydrophobic compound intended to form the terminal hydrophobic groups of the polymer of formula (A).

This compound consists of a hydrophobic group and a functional group containing a labile hydrogen, for example a hydroxyl, primary or secondary amine, or thiol functional group.

By way of example, this compound may be a fatty alcohol, such as in particular stearyl alcohol, dodecyl alcohol, and decyl alcohol. When this compound contains a polymeric chain, it may be for example a hydroxyl hydrogenated polybutadiene.

The hydrophobic group of the polyurethane of formula (A) may also result from the quatemization reaction of the tertiary amine of the compound containing at least one tertiary amine unit. Thus, the hydrophobic group is introduced by the quatemizing agent. This quaternizing agent is a compound of the RQ or R'Q type, in which R and R' are as defined above and Q denotes a leaving group such as a halide, a sulfate, and the like.

The cationic associative polyurethane thickener may additionally comprise a hydrophilic sequence. This sequence is provided by a fourth type of compound entering into the preparation of the polymer. This compound may be multifunctional. It is preferably difunctional. It is also possible to have a mixture where the percentage of multifunctional compound is low.

The functional groups containing a labile hydrogen are alcohol, primary or secondary amine, or thiol functional groups. This compound may be a polymer terminated at the chain ends by one of these functional groups containing a labile hydrogen.

By way of example, there may be mentioned, when polymers are not involved, ethylene glycol, diethylene glycol and propylene glycol.

In the case of a hydrophilic polymer, there may be mentioned, by way of example, polyethers, sulfonated polyesters, sulfonated polyamides, or a mixture of these polymers. Preferably, the hydrophilic compound is a polyether and in particular a polyethylene oxide or a polypropylene oxide.

The hydrophilic group noted Y in formula (A) is optional. Indeed, the units containing a quaternary or protonated amine functional group may suffice to provide the solubility or water-dispersibility necessary for this type of polymer in an aqueous solution. Although the presence of a hydrophilic group Y is optional, cationic associative polyurethane thickeners are nevertheless preferred which contain such a group.

The associative polyurethane thickener used in the present invention may also be nonionic, in particular nonionic polyurethane-polyethers. The nonionic polyurethane-polyethers may have both at least one hydrophilic moiety and at least one hydrophobic moiety. More particularly, said polymers may contain in their chain both hydrophilic sequences most often of a polyoxyethylenated nature and hydrophobic sequences which may be aliphatic linkages alone and/or cycloaliphatic and/or aromatic linkages.

Preferably, these polyether-polyurethanes comprise at least two lipophilic hydrocarbon chains, having from 6 to 30 carbon atoms, preferably from 6 to 20, separated by a hydrophilic sequence, it being possible for the hydrocarbon chains to be pendent chains or chains at the end of a hydrophilic sequence. In particular, it is possible for one or more pendent chains to be envisaged. In addition, the polymer may comprise a hydrocarbon chain at one end or at both ends of a hydrophilic sequence.

The polyether-polyurethanes may be polyblocks, in particular in triblock form. The hydrophobic sequences may be at each end of the chain (for example: triblock copolymer with hydrophilic central sequence) or distributed both at the ends and in the chain (polyblock copolymers for example). These same polymers may also be in the form of graft units or may be star-shaped.

The associative polyurethane thickener can form a network in water in which the hydrophobic part connects quasi-micelles as shown in FIG. 1.

Therefore, the associative polyurethane thickeners can increase viscosity or consistency of the composition according to the present invention. Thus, after application of the composition according to the present invention, it can recover the original elasticity of the composition quickly.

The nonionic polyether-polyurethanes containing a fatty chain may be triblock copolymers whose hydrophilic sequence is a polyoxyethylenated chain comprising from 50 to 1000 oxyethylenated groups.

The nonionic polyether-polyurethanes comprise a urethane bond between the hydrophilic sequences, hence the origin of the name.

By extension, those whose hydrophilic sequences are linked by other chemical bonds to the hydrophobic sequences are also included among the nonionic polyether-polyurethanes containing a hydrophobic chain.

By way of examples of nonionic polyether-polyurethanes containing a hydrophobic chain which can be used in the present invention, it is also possible to use Rheolate® 205 containing a urea functional group sold by the company RHEOX or else the Rheolates® 208, 204 or 212, as well as Acrysol RM 184®.

There may also be mentioned the product ELFACOS T210® containing a $C_{12}$-$C_{14}$ alkyl chain and the product ELFACOS T212® containing a $C_{18}$ alkyl chain from AKZO.

The product DW 1206B® from ROHM & HAAS containing a $C_{20}$ alkyl chain and with a urethane bond, sold at 20% dry matter content in water, may also be used.

It is also possible to use solutions or dispersions of these polymers in particular in water or in an aqueous-alcoholic medium. By way of examples of such polymers, there may be mentioned Rheolate® 255, Rheolate® 278 and Rheolate® 244 sold by the company RHEOX. It is also possible to use the product DW 1206F and DW 1206J provided by the company ROHM & HAAS.

The above-described polyether-polyurethanes which can be used can also be chosen from those described in the article by G. Fonnum, J. Bakke and Fk. Hansen-Colloid Polym. Sci 271, 380-389 (1993).

As the above-described polyether-polyurethanes, mention may be made of polyurethane-polyethers comprising in their chain at least one polyoxyethylenated hydrophilic block and at least one of hydrophobic blocks containing at least one sequence chosen from aliphatic sequences, cycloaliphatic sequences, and aromatic sequences.

It may be preferable that the polyurethane-polyethers comprise at least two hydrocarbon-based lipophilic chains having from 8 to 30 carbon atoms, separated by a hydrophilic block, and wherein the hydrocarbon-based chains are chosen from pendent chains and chains at the end of the hydrophilic block.

According to a specific form of the present invention, use will be made of a polyurethane/polyether that may be obtained by polycondensation of at least three compounds comprising (i) at least one polyethylene glycol comprising from 150 to 180 mol of ethylene oxide, (ii) a polyoxyethylenated stearyl alcohol comprising 100 mol of ethylene oxide, and (iii) a diisocyanate.

Such polyurethane/polyethers are sold especially by the company Element is under the name Rheolate FX 1100® and Rheoluxe 811®, which is a polycondensate of polyethylene glycol containing 136 mol of ethylene oxide, of stearyl alcohol polyoxyethylenated with 100 mol of ethylene oxide and of hexamethylene diisocyanate (HDI) with a weight-average molecular weight of 40000 (INCI name: PEG-136/Steareth-100/HDI Copolymer).

According to another specific form of the present invention, use will be made of a polyurethane/polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane/polyethers are sold in particular by the company Rohm & Haas under the names Aculyn 46® and Aculyn 44®.

Aculyn 46® having the INCI name: PEG-150/Stearyl Alcohol/SMDI Copolymer, is a polycondensate of polyethylene glycol comprising 150 or 180 mol of ethylene oxide, of stearyl alcohol and of methylenebis(4-cyclohexyl isocyanate) (SMDI) at 15% by weight in a matrix of maltodextrin (4%) and water (81%) (INCI name: PEG-150/Stearyl Alcohol/SMDI Copolymer).

Aculyn 44® (PEG-150/Decyl Alcohol/SMDI Copolymer) is a polycondensate of polyethylene glycol comprising 150 or 180 mol of ethylene oxide, of decyl alcohol and of methylenebis(4-cyclohexyl isocyanate) (SMDI) at 35% by weight in a mixture of propylene glycol (39%) and water (26%) (INCI name: PEG-150/Decyl Alcohol/SMDI Copolymer).

As the associative polyurethanes, it may be preferable to use a compound represented by the following formula (1):

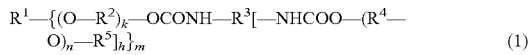

(1)

wherein $R^1$ represents a hydrocarbon group, $R^2$ and $R^4$ independently represent alkylene groups having 2 to 4 carbon atoms, which alkylene groups may be identical or different from each other, or a phenylethylene group, $R^3$ represents a hydrocarbon group, which may optionally have a urethane bond, $R^5$ represents a branched chain or secondary hydrocarbon group, m represents a number of at least 2, h represents a number of at least 1, k represents a number within the range of 1 to 500, and n represents a number within the range of 1 to 200.

The hydrophobically modified polyurethane that is represented by the general formula (1) shown above is obtained by, for example, reacting at least one polyether polyol that is represented by the formula $R^1$—$[(O$—$R^2)_k$—$OH]_m$, at least one polyisocyanate that is represented by the formula $R^3$—$(NCO)_{h+1}$, and at least one polymonoalcohol that is represented by the formula HO—$(R^4$—$O)_n$—$R^5$.

In such cases, $R^1$ to $R^5$ in the general formula (1) are determined by the compounds $R^1$—$[(O$—$R^2)_k$—$OH]_m$, $R^3$—$(NCO)_{h+1}$ and HO—$(R^4$—$O)_n$—$R^5$. The loading ratios among the three compounds are not limited particularly and should preferably be such that the ratio of the isocyanate group derived from the polyisocyanate to the hydroxyl group derived from the polyether polyol and the polyether monoalcohol is selected within the range of NCO/OH of between 0.8:1 and 1.4:1.

The polyether polyol compound that is represented by the formula $R^1$—$[(O$—$R^2)_k$—$OH]_m$ and that may be used preferably for obtaining the associative thickener represented by the general formula (1) may be obtained from addition polymerization of an m-hydric polyol with an alkylene oxide, such as ethylene oxide, propylene oxide, butylene oxide, or epichlorohydrin, or with styrene oxide, and the like.

The polyols should preferably be di- to octa-hydric polyols. Examples of the di- to octa-hydric polyols include dihydric alcohols, such as ethylene glycol, propylene glycol, butylene glycol, hexamethylene glycol, and neopenthyl glycol; trihydric alcohols, such as glycerol, trioxy isobutane, 1,2,3-butanetriol, 1,2,3-pentanetriol, 2-methyl-1,2,3-propanetriol, 2-methyl-2,3,4-butanetriol, 2-ethyl-1,2,3-butanetriol, 2,3,4-pentanetriol, 2,3,4-hexanetriol, 4-propyl-3,4,5-heptanetriol, 2,4-dimethyl-2,3,4-pentanetriol, pentamethylglycerol, pentaglycerol, 1,2,4-butanetriol, 1,2,4-pentanetriol, trimethylolethane, and trimethylolpropane; tetrahydric alcohols, such as pentaerythritol, 1,2,3,4-pentanetetrol, 2,3,4,5-hexanetetrol, 1,2,4,5-pentanetetrol, and 1,3,4,5-hexanetetrol; pentahydric alcohols, such as adonitol, arabitol, and xylitol; hexahydric alcohols, such as dipentaerythritol, sorbitol, mannitol, and iditol; and octahydric alcohols, such as sucrose.

Also, $R^2$ is determined by the alkylene oxide, styrene oxide, or the like, which is subjected to the addition. Particularly, for availability and excellent effects, an alkylene oxide having 2 to 4 carbon atoms, or styrene oxide is preferable.

The alkylene oxide, styrene oxide, or the like, to be subjected to the addition may be subjected to single polymerization, or random polymerization or block polymerization of at least two members. The procedure for the addition may be a conventional procedure. Also, the polymerization degree k may be selected within the range of 0 to 1,000, preferably within the range of 1 to 500, and more preferably within the range of 10 to 200. Further, the ratio of the ethylene group occupying $R^2$ should preferably be within the range of 50 to 100 mass % with respect to the total quantity of $R^2$. In such cases, the associative thickener appropriate for the purposes of the present invention is obtained.

Furthermore, the molecular weight of the polyether polyol compound that is represented by the formula $R^1$—$[(O$—$R^2)_k$—$OH]_m$, should preferably be selected within the range of 500 to 100,000, and should more preferably be selected within the range of 1,000 to 50,000.

The polyisocyanate that is represented by the formula $R^3$—$(NCO)_{h+1}$ and that may be used preferably for obtaining the hydrophobically modified polyether urethane represented by the general formula (1) employed in accordance with the present invention is not limited particularly in so far as the polyisocyanate has at least two isocyanate groups in the molecule. Examples of the polyisocyanates include aliphatic diisocyanates, aromatic diisocyanates, alicyclic diisocyanates, biphenyl diisocyanate, phenylmethane diisocyanate, phenylmethane triisocyanate, and phenylmethane tetraisocyanate.

Also, it is possible to employ dimers and trimers (isocyanurate bonds) of the above-enumerated polyisocyanates. Further, it is possible to employ biuret obtained by a reaction with an amine.

Furthermore, it is possible to employ a polyisocyanate having a urethane bond obtained by a reaction of the aforesaid polyisocyanate compound and a polyol. As the polyol, di- to octa-hydric polyols are preferable, and the above-enumerated polyols are preferable. In cases where a tri- or higher-hydric polyisocyanate is used as the polyisocyanate that is represented by the formula $R^3$—$(NCO)_{n+1}$, it is preferable to employ the aforesaid polyisocyanate having the urethane bond.

The polyether monoalcohol that is represented by the formula HO—$(R^4$—$O)_n$—$R^5$ and that may be used preferably for obtaining the hydrophobically modified polyether urethane represented by the general formula (1) employed in accordance with the present invention is not limited particularly in so far as the polyether monoalcohol is a polyether of a straight chain, branched chain, or secondary monohydric alcohol. The polyether monoalcohol may be obtained by addition polymerization of the straight chain, branched chain, or secondary monohydric alcohol with an alkylene oxide, such as ethylene oxide, propylene oxide, butylene oxide, or epichlorohydrin, or with styrene oxide, and the like.

The compound represented by the general formula (1) may be produced by, for example, heating at a temperature of 80 to 90° C. for 1 to 3 hours and thereby causing a reaction to occur in the same manner as that in the ordinary reaction of a polyether and an isocyanate.

As the compound represented by the general formula (1), polyethyleneglycol-240/decyltetradeceth-20/hexamethylene diisocyanate copolymer is preferable.

The polyethyleneglycol-240/decyltetradeceth-20/hexamethylene diisocyanate copolymer is referred to also as PEG-240/HDI copolymer bis-decyltetradeceth-20 ether.

According to the present invention, it is preferable that the associative polyurethane thickener be selected from Steareth-100/PEG-136/HDI Copolymer sold by the company Rheox under the name of Rheolate FX 1100, PEG-240/HDI Copolymer Bis-decyltetradeceth-20 ether sold by the company Asahi Denka under the name of Adekanol GT-700, and mixtures thereof.

(ii) Among the crosslinked acrylic acid homopolymers that may be mentioned are those crosslinked with an allylic alcohol ether of the sugar series. Mention may be made of carbomer, which is a homopolymer of acrylic acid crosslinked with an allyl ether of pentaerythritol, an allyl ether of sucrose, or an allyl ether of propylene, such as the products sold under the names Carbopol 980, 981, 954, 2984, and 5984 by the company Lubrizol or the products sold under the names Synthalen M and Synthalen K by the company 3 VSA.

(iii) The crosslinked copolymers of (meth)acrylic acid and of $C_1$-$C_6$ alkyl acrylate can be chosen from crosslinked copolymers of methacrylic acid and of ethyl acrylate as an aqueous dispersion comprising 38% active material sold, for example, under the name Viscoatex 538C by the company Coatex, and crosslinked copolymers of acrylic acid and of ethyl acrylate as an aqueous dispersion comprising 28% active material sold under the name Aculyn 33 by the company Rohm & Haas. Crosslinked copolymers of methacrylic acid and of ethyl acrylate include an aqueous dispersion comprising 30% active material sold under the name CARBOPOL AQUA SF-1 by the company NOVEON.

(iv) Among the nonionic homopolymers or copolymers comprising ethylenically unsaturated monomers of ester and/or amide type, mention may be made of the products sold under the names: Cyanamer P250 by the company Cytec (polyacrylamide); PMMA MBX-8C by the company US Cosmetics (methyl methacrylate/ethylene glycol dimethacrylate copolymer); Acryloid B66 by the company Rohm & Haas (butyl methacrylate/methyl methacrylate copolymer); and BPA 500 by the company Kobo (polymethyl methacrylate).

(v) Ammonium acrylate homopolymers that may be mentioned include the product sold under the name Microsap PAS 5193 by the company Hoechst.

Copolymers of ammonium acrylate and of acrylamide include the product sold under the name Bozepol C Nouveau or the product PAS 5193 sold by the company Hoechst (which are described and prepared in documents FR-2 416 723, U.S. Pat. Nos. 2,798,053, and 2,923,692).

(vi) The polysaccharides are, for example, chosen from glucans, modified and unmodified starches (such as those derived, for example, from cereals, for instance wheat, corn, or rice, from vegetables, for instance yellow peas, and tubers, for instance potatoes or cassava), amylose, amylopectin, glycogen, dextrans, celluloses, and derivatives thereof (e.g., methylcelluloses, hydroxyalkylcelluloses, ethyl hydroxyethylcelluloses, and carboxymethylcelluloses), mannans, xylans, lignins, arabans, galactans, galacturonans, chitin, chitosans, glucuronoxylans, arabinoxylans, xyloglucans, glucomannans, pectic acids, and pectins, alginic acid and alginates, arabinogalactans, carrageenans, agars, glycosaminoglucans, gum arabics, gum tragacanths, ghatti gums, karaya gums, carob gums, galactomannans, such as guar gums, and nonionic derivatives thereof (e.g., hydroxypropyl guar), and xanthan gums, and mixtures thereof.

For example, the polysaccharides that may be used are chosen from those described, for example, in "Encyclopedia of Chemical Technology", Kirk-Othmer, Third Edition, 1982, volume 3, pp. 896-900, and volume 15, pp. 439-458, in "Polymers in Nature" by E. A. MacGregor and C. T. Greenwood, published by John Wiley & Sons, Chapter 6, pp. 240-328, 1980, and in "Industrial Gums-Polysaccharides and their Derivatives", edited by Roy L. Whistler, Second Edition, published by Academic Press Inc., the content of these three publications being entirely incorporated by reference.

For example, starches, guar gums, celluloses, and derivatives thereof can be used.

Among the starches that may be used, mention may be made, for example, of macromolecules in the form of polymers comprising base units which are anhydroglucose units. The number of these units and their assembly make it possible to distinguish between amylose (linear polymer) and amylopectin (branched polymer). The relative proportions of amylose and amylopectin, as well as their degree of polymerization, can vary according to the botanical origin of the starches.

The molecules of starches used may have cereals or tubers as their botanical origin. Thus, the starches can be, for example, chosen from maize, rice, cassava, tapioca, barley, potato, wheat, sorghum, and pea starches.

Starches generally exist in the form of a white powder, insoluble in cold water, whose elementary particle size ranges from 3 to 100 microns.

The starches may be optionally $C_1$-$C_6$ hydroxyalkylated or $C_1$-$C_6$ acylated (such as acetylated). The starches may have also undergone heat treatments.

Distarch phosphates or compounds rich in distarch phosphate, such as the product provided under the references PREJEL VA-70-T AGGL (gelatinized hydroxypropylated cassava distarch phosphate) or PREJEL TK1 (gelatinized cassava distarch phosphate) or PREJEL 200 (gelatinized acetylated cassava distarch phosphate) by the company AVEBE, may also be used.

The guar gums can be modified or unmodified.

The unmodified guar gums are, for example, the products sold under the name Vidogum GH 175 by the company Unipectine and under the names Meypro-Guar 50 and Jaguar C by the company Meyhall.

The modified nonionic guar gums are, for example, modified with $C_1$-$C_6$ hydroxyalkyl groups.

Among the hydroxyalkyl groups that may be mentioned, for example, are hydroxymethyl, hydroxyethyl, hydroxypropyl, and hydroxybutyl groups.

These guar gums are well known in the prior art and can be prepared, for example, by reacting the corresponding alkene oxides such as propylene oxides, with the guar gum so as to obtain a guar gum modified with hydroxypropyl groups.

The degree of hydroxyalkylation, which corresponds to the number of alkylene oxide molecules consumed by the number of free hydroxyl functions present on the guar gum, may, for example, range from 0.4 to 1.2.

Such nonionic guar gums optionally modified with hydroxyalkyl groups are sold, for example, under the trade names Jaguar HP8, Jaguar HP60, Jaguar HP120, Jaguar DC 293, and Jaguar HP 105 by the company Rhodia Chimie (Meyhall) or under the name Galactasol $4H_{4FD2}$ by the company Aqualon.

Among the celluloses and cellulose derivatives, such as cellulose modified with hydroxylalkyl groups, that are used are, for example, hydroxypropylmethylcellulose, hydroxyethylcellulose, and hydroxypropylcelluloses, as well as hydrophobicized hydroxypropylmethylcellulose. Mention may be made of the products sold under the names Klucel E F, Klucel H, Klucel L H F, Klucel M F, and Klucel G by the company Aqualon.

(vii) The fatty alcohols are, for example, chosen from myristyl alcohol, cetyl alcohol, stearyl alcohol, and behenyl alcohol.

The amount of the (d) thickener(s) in the composition according to the present invention may be 0.001% by weight or more, preferably 0.005% by weight or more, and more preferably 0.01% by weight or more, relative to the total weight of the composition. It may be even more preferable that the amount of the (d) thickener(s) in the composition according to the present invention be 0.1% by weight or more, relative to the total weight of the composition.

On the other hand, the amount of the (d) thickener(s) in the composition according to the present invention may be 20% by weight or less, preferably 10% by weight or less, and more preferably 5% by weight or less, relative to the total weight of the composition. It may be even more preferable that the amount of the (d) thickener(s) in the composition according to the present invention be 1% by weight or less, relative to the total weight of the composition.

The amount of the (d) thickener(s) in the composition according to the present invention may range from 0.001 to 20% by weight, preferably from 0.005 to 10% by weight, more preferably from 0.01 to 5% by weight, relative to the total weight of the composition. It may be even more preferable that the amount of the (d) thickener(s) in the composition according to the present invention be from 0.1% to 1% by weight, relative to the total weight of the composition.

[Water]

The composition according to the present invention may comprise water.

The amount of water in the composition according to the present invention may be 50% by weight or more, preferably 60% by weight or more, and more preferably 70% by weight or more, relative to the total weight of the composition. It may be even more preferable that the amount of water in the composition according to the present invention be 80% by weight or more, relative to the total weight of the composition.

On the other hand, the amount of water in the composition according to the present invention may be 98% by weight or less, preferably 95% by weight or less, and more preferably 90% by weight or less, relative to the total weight of the composition. It may be even more preferable that the amount of water in the composition according to the present invention be 85% by weight or less, relative to the total weight of the composition.

The amount of water in the composition according to the present invention may range from 50 to 98% by weight, preferably from 60 to 95% by weight, more preferably from 70 to 90% by weight, relative to the total weight of the composition. It may be even more preferable that the amount of water in the composition according to the present invention be from 80% to 85% by weight, relative to the total weight of the composition.

[Fatty Acid]

The composition according to the present invention may comprise at least one fatty acid. A single type of fatty acid may be used, but two or more different types of fatty acids may be used in combination.

A fatty acid here means an aliphatic monocarboxylic acid, preferably an aliphatic monocarboxylic acid having a long carbon chain. It is preferable that the fatty acid have at least 6 carbon atoms, preferably 7 carbon atoms, and more preferably 8 carbon atoms. The fatty acid may preferably comprise up to 30 carbon atoms, and more preferably up to 20 carbon atoms.

The fatty acid may be selected from saturated or unsaturated, linear or branched fatty acids. As the unsaturated, linear or branched fatty acids, mono-unsaturated, linear or branched fatty acids or polyunsaturated, linear or branched fatty acids may be used. As the unsaturated moiety of the unsaturated, linear or branched fatty acids, a carbon-carbon double bond or a carbon-carbon triple bond may be mentioned.

As the fatty acid, for example, a $C_{8-30}$ saturated, linear or branched fatty acid may be used. As $C_{8-30}$ saturated, linear or branched fatty acids other than lauric acid, mention may be made of caprylic acid ($C_8$), pelargonic acid ($C_9$), capric acid ($C_{10}$), lauric acid ($C_{12}$), myristic acid ($C_{14}$), pentadecanoic acid ($C_{15}$), palmitic acid ($C_{16}$), heptadecanoic acid ($C_{17}$), stearic acid ($C_{18}$), nonadecanoic acid ($C_{19}$), arachidic acid ($C_{20}$), behenic acid ($C_{22}$), and lignoceric acid ($C_{24}$).

On the other hand, as the fatty acid, for example, a $C_{8-30}$ unsaturated, linear or branched fatty acid may also be used. As the $C_{8-30}$ unsaturated, linear or branched fatty acids, mention may be made of palmitoleic acid ($C_{16}$), oleic acid ($C_{18}$), linoleic acid ($C_{18}$), linolenic acid ($C_{18}$), arachidonic acid ($C_{20}$), and nervonic acid ($C_{24}$).

It is preferable that the fatty acid be a linear or branched, in particular saturated, fatty acid having a carbon chain length of $C_{10-30}$.

It is more preferable that the fatty acid be selected from $C_{13-18}$ fatty acids, preferably $C_{13-18}$ saturated, linear or branched fatty acids. Thus, more preferable fatty acids are myristic acid, pentadecanoic acid, palmitic acid, heptadecanoic acid, and stearic acid. Myristic acid, palmitic acid, and stearic acid are even more preferable.

The fatty acid may be in the form of a free acid or in the form of a salt thereof. As a salt of the fatty acid, mention may be made of an inorganic salt such as an alkali metal salt (a sodium salt, a potassium salt, or the like) and an alkaline earth metal salt (a magnesium salt, a calcium salt, or the like); and an organic salt such as an ammonium salt (a quaternary ammonium salt or the like) and an amine salt (a triethanolamine salt, a triethylamine salt, or the like). A single type of fatty acid salt or a combination of different types of fatty acid salts may be used. Further, a combination of one or more fatty acids in the form of a free acid and one or more fatty acids in the form of a salt may be used, in which one or more types of salts may also be used. It is preferable that at least a part (preferably at least 80%, and more preferably 90%), in particular all, of the fatty acids be in the form of a free acid.

The amount of the fatty acid(s) in the composition according to the present invention may range from 0.00001 to 1% by weight, preferably from 0.00003 to 0.1% by weight, more preferably from 0.00005 to 0.01% by weight, relative to the total weight of the composition. It may be even more preferable that the amount of the fatty acid(s) in the composition according to the present invention be from 0.00008% to 0.001% by weight, relative to the total weight of the composition.

[Polyol]

The composition according to the present invention may further comprise at least one polyol. A single type of polyol may be used, but two or more different types of polyol may be used in combination.

The term "polyol" here means an alcohol having two or more hydroxy groups, and does not encompass a saccharide or a derivative thereof. The derivative of a saccharide includes a sugar alcohol which is obtained by reducing one or more carbonyl groups of a saccharide, as well as a saccharide or a sugar alcohol in which the hydrogen atom or atoms in one or more hydroxy groups thereof has or have been replaced with at least one substituent such as an alkyl group, a hydroxyalkyl group, an alkoxy group, an acyl group or a carbonyl group.

The polyol may be a $C_2$-$C_{12}$ polyol, preferably a $C_2$-$C_9$ polyol, comprising at least 2 hydroxy groups, and preferably 2 to 5 hydroxy groups.

The polyol may be a natural or synthetic polyol. The polyol may have a linear, branched or cyclic molecular structure.

The polyol may be selected from glycerins and derivatives thereof, and glycols and derivatives thereof. The polyol may be selected from the group consisting of glycerin, diglycerin, polyglycerin, ethyleneglycol, diethyleneglycol, propyleneglycol, dipropyleneglycol, butyleneglycol, pentyleneglycol, hexyleneglycol, 1,3-propanediol, 1,5-pentanediol, polyethyleneglycol (5 to 50 ethyleneoxide groups), and sugars such as sorbitol.

The amount of the polyol(s) in the composition according to the present invention may range from 0.01 to 35% by weight, preferably from 0.1 to 30% by weight, more preferably from 1 to 25% by weight, relative to the total weight of the composition. It may be even more preferable that the amount of the polyol(s) in the composition according to the present invention be from 5 to 20% by weight, relative to the total weight of the composition.

[Other Ingredients]

The compositions in accordance with the present invention may also comprise one or more standard cosmetic adjuvants chosen from oils, waxes, organic solvents, UV-screening agents, softeners, humectants, opacifiers, stabilizers, emollients, silicones, antifoams, fragrances, preserving agents, cationic or amphoteric surfactants, active agents, fillers, colouring agents, cationic polymers, propellants, acidifying or basifying agents, or any other ingredient usually used in cosmetics and/or dermatology.

Needless to say, a person skilled in the art will take care to select the optional adjuvant(s) added to the composition according to the invention such that the advantageous properties intrinsically associated with the composition in accordance with the invention are not, or are not substantially, adversely affected by the envisaged addition.

In particular, the composition according to the present invention may further comprise at least one organic solvent. So the organic solvent is preferably water miscible. As the organic solvent, there may be mentioned, for example, $C_1$-$C_4$ alkanols, such as ethanol and isopropanol; aromatic alcohols such as benzyl alcohol and phenoxyethanol; analogous products; and mixtures thereof.

The organic water-soluble solvents may be present in an amount ranging from less than 10% by weight, preferably from 5% by weight or less, and more preferably from 1% by weight or less, relative to the total weight of the composition.

[Preparation]

The composition according to the present invention can be prepared by mixing the above essential and optional ingredients in accordance with a conventional process. The conventional process includes mixing with a homogenizer, for example a turbine mixer.

[Process and Use]

It is preferable that the composition according to the present invention be a cosmetic composition, preferably a cosmetic composition for a keratin substance such as skin.

The composition according to the present invention can be used for a non-therapeutic process, such as a cosmetic process, for treating a keratin substance such as skin, hair, mucous membranes, nails, eyelashes, eyebrows and/or scalp, by being applied to the keratin substance.

Thus, the present invention also relates to a cosmetic process for treating a keratin substance, comprising the step of applying the composition according to the present invention to the keratin substance.

It is preferable that the composition according to the present invention is used as a so-called auto-pump product. In the auto-pump product, the composition according to the present invention may be contained in a container with a dispenser which has an outlet and can mix air with the composition to form foam when the composition in the container is discharged from the outlet of the dispenser. The auto-pump products which do not contain gas, and therefore are preferable from an environmental view point than so-called aerosol type products using a propellant gas, and the transportation of the auto-pump product is easier than that of the aerosol type products.

The present invention may also relate to a use of the composition according to the present invention as a cosmetic product or in a cosmetic product such as care products for the skin such as body and/or face and/or mucous membranes such as lips and/or the scalp and/or the hair and/or the nails and/or the eyelashes and/or the eyebrows. The care product may be a lotion or a cosmetic water, a cream, a serum, a hair tonic, a hair conditioner, a sun screening agent, and the like.

In other words, the composition according to the present invention can be used, as it is, as a cosmetic product. Alternatively, the composition according to the present invention can be used as an element of a cosmetic product. For example the composition according to the present invention can be added to or combined with any other elements to form a cosmetic product.

The composition according to the present invention includes a combination of surfactants, and therefore, is foamable or foaming. However, the foam which can be prepared by the composition according to the present invention may be used not for cleansing but for providing good feeling to use such as sparkling feeling. Accordingly, the composition according to the present invention may be used as a care product (e.g., skin care cosmetics such as a lotion or cosmetic water) or in care products, and may not be used as a cleansing product or in cleansing products.

Another aspect of the present invention may be use of a combination of:
(a) at least one first anionic surfactant selected from glutamic acid compounds and salts thereof;
(b) at least one second anionic surfactant selected from alanine compounds and salts thereof, glycine compounds and salts thereof, and mixtures thereof;
(c) at least one nonionic surfactant; and
(d) at least one thickener,
in a composition in order to make the composition stable and be capable of forming foam with good quality such as: the foam has fine cells, the foam can provide a sparkling sensation when the foam breaks, and the foam can last for a long period of time.

EXAMPLES

The present invention will be described in more detail by way of examples, which however should not be construed as limiting the scope of the present invention.

Examples 1-3 and Comparative Examples 1-8

The following compositions according to Examples 1-3 and Comparative Examples 1-8, shown in Table 1, were prepared by mixing the components shown in Table 1. The numerical values for the amounts of the components shown in Table 1 are all based on "% by weight" as active raw materials.

[Evaluations]
{Foam Quality}
5 professional panelists evaluated "fineness", "sparkling" and "lasting" of foam for the compositions according to Examples 1-3 and Comparative Examples 1-8.

Each of the compositions according to Examples 1-3 and Comparative Examples 1-8 was charged into a bottle with a foaming device, and discharged or dispensed onto the hands of the panelists to form a foam. The same type of bottle and the foaming device were used for the compositions according to Examples 1-3 and Comparative Examples 1-8.

The panelists observed and touched the foam to evaluate "fineness", "sparkling" and "lasting" as follows.
(Fineness)
The panelists observed the foam just after being formed, and evaluated the fineness of the foam cells in accordance with the following score criteria:
Very fine foam cells: 5
Fine foam cells: 4
Medium size foam cells: 3
Rough foam cells: 2
Very rough foam cells: 1
The scores were averaged, and classified in accordance with the following criteria:
Good: more than 3 and 5 or less
Poor: 1 or more and 3 or less
The results are shown in Table 1.
(Sparkling)
The panelists touched the foam just after being formed, and broke the foam to evaluate the sparkling sensation provided by the broken foam in accordance with the following score criteria:
Very strong sparkling sensation: 5
Strong sparkling sensation: 4
Medium sparking sensation: 3

TABLE 1

| Ingredients | Ex. 1 | Ex. 2 | Ex. 3 | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 |
|---|---|---|---|---|---|---|---|---|---|---|---|
| Water | qsp 100 | qsp 100 | qsp 100 | qsp 100 | qsp 100 | qsp 100 | qsp 100 | qsp 100 | qsp 100 | qsp 100 | qsp 100 |
| Glycerin | 10 | 10 | 10 | 10 | 10 | 10 | 10 | 10 | 10 | 10 | 10 |
| Butylene Glycol | 4 | 4 | 4 | 4 | 4 | 4 | 4 | 4 | 4 | 4 | 4 |
| Dipropylene Glycol | 2 | 2 | 2 | 2 | 2 | 2 | 2 | 2 | 2 | 2 | 2 |
| (a) Disodium Cocoyl Glutamate (and) Sodium Cocoyl Glutamate (AMISOFT CS 22)*1 | 0.125 | 0.125 | 0.125 | — | 0.125 | 0.125 | 0.125 | 0.125 | — | — | — |
| (b) Sodium Cocoyl Alaninate (AMILITE ACS-12)*2 | 0.03 | — | — | 0.03 | — | 0.03 | 0.03 | 0.03 | — | — | — |
| (b) Sodium Cocoyl Glycinate (AMILITE GCS-12K)*3 | — | 0.03 | 0.03 | — | — | — | — | — | — | — | — |
| Phenoxyethanol | 0.7 | 0.7 | 0.7 | 0.7 | 0.7 | 0.7 | 0.7 | 0.7 | 0.7 | 0.7 | 0.7 |
| (c) PPG-6 Decyltetradeceth-30 | 0.3 | 0.3 | 0.3 | 0.3 | 0.3 | — | 0.3 | — | 0.3 | — | — |
| (d) PEG-240/HDI Copolymer Bis-Decyltetradeceth-20 Ether | 0.3 | 0.3 | — | 0.3 | 0.3 | 0.3 | — | — | — | 0.3 | — |
| (d) Carbomer (CARBOPOL 981 POLYMER by LUBRIZOL) | — | — | 0.1 | — | — | — | — | — | — | — | — |
| Foam Quality    Fineness | Good | Good | Good | Poor | Poor | Good | Good | Good | Poor | Poor | Poor |
| Sparkling | Good | Good | Good | Good | Good | Good | Good | Good | Good | Poor | Good |
| Lasting | Good | Good | Good | Poor | Poor | Good | N.E.*4 | Poor | Poor | Poor | Poor |
| Stability | Good | Good | Good | Good | Good | Poor | Good | Poor | Good | Good | Good |

*1AMISOFT CS 22 by Ajinomoto: WATER 75%, DISODIUM COCOYL GLUTAMATE 20.2%, SODIUM COCOYL GLUTAMATE 4.8%
*2AMILITE ACS-12 by Ajinomoto: WATER 70%, SODIUM COCOYL ALANINATE 30%
*3AMILITE GCS-12K by Ajinomoto: WATER 70%, SODIUM COCOYL GLYCINATE 30%
*4N.E.: Not Enough
The values shown in Table 1 above are % by weight of active raw materials.

Weak sparkling sensation: 2
No sparkling sensation: 1
The scores were averaged, and classified in accordance with the following criteria:
Good: more than 3 and 5 or less
Poor: 1 or more and 3 or less
The results are shown in Table 1.
(Lasting)
The panelists observed the foam just after being formed, and evaluated the lasting of the shape of the foam in accordance with the following score criteria:
Very long lasting: 5
Long lasting: 4
Medium lasting: 3
Short lasting: 2
Very Short lasting: 1
The scores were averaged, and classified in accordance with the following criteria:
Good: more than 4 and 5 or less
Not Enough: more than 3 and 4 or less
Poor: 1 or more and 3 or less
The results are shown in Table 1.
{Stability}
Each of the compositions according to Examples 1-3 and Comparative Examples 1-8 was charged into a transparent glass bottle, and maintained for 10 days under the temperature change condition of from −20° C. to 20° C. in a day. The aspect of each bottle was evaluated in accordance with the following criteria:
Good: almost the same conditions as production
Poor: white sedimentation was observed
The results are shown in Table 1.

It is clear from Table 1 that the compositions according to Examples 1-3 which comprise the ingredients (a) to (d), shown in Table 1, corresponding to those recited in claim 1 are stable and can form foam with good quality. It is also clear from Examples 1 and 2 that an anionic surfactant based on an alanine compound salt such as sodium cocoyl alaninate and another anionic surfactant based on glycine compound salt such as sodium cocoyl glycinate are interchangeable.

On the other hand, Table 1 shows:
The composition according to Comparative Example 1 which lacks the ingredient (a) (first anionic surfactant) cannot provide long-lasting foam with fine cells;
The composition according to Comparative Example 2 which lacks the ingredient (b) (second anionic surfactant) cannot provide long-lasting foam with fine cells;
The composition according to Comparative Example 3 which lacks the ingredient (c) (nonionic surfactant) cannot be stable over time;
The composition according to Comparative Example 4 which lacks the ingredient (d) (thickener) cannot provide sufficiently-lasting foam;
The composition according to Comparative Example 5 which lacks the ingredients (c) and (d) cannot be stable over time, and cannot provide long-lasting foam;
The composition according to Comparative Example 6 which lacks the ingredients (a), (b) and (d) cannot provide long-lasting foam with fine cells;
The composition according to Comparative Example 7 which lacks the ingredients (a), (b) and (c) cannot provide foam with good quality such as fine cells, sparkling sensation and long-lasting;
The composition according to Comparative Example 8 which lacks the ingredients (a), (b), (c) and (d) cannot provide long-lasting foam with fine cells.

The invention claimed is:

1. A composition comprising:
(a) at least one first anionic surfactant selected from cocoyl or lauroyl glutamic acid and salts thereof;
(b) at least one second anionic surfactant selected from cocoyl or lauroyl alanine and salts thereof, cocoyl or lauroyl glycine and salts thereof, and mixtures thereof;
(c) at least one nonionic surfactant; and
(d) at least one thickener selected from crosslinked acrylic acid homopolymers and polyurethane/polyethers comprising in their chain at least one polyoxyethylenated hydrophilic block and at least one of hydrophobic blocks containing at least one sequence chosen from aliphatic sequences, cycloaliphatic sequences, and aromatic sequences, and mixtures thereof,
wherein the nonionic surfactant comprises a polyoxyethylenated (15-40 EO) and polyoxypropylenated (5-30 PO) alkyl ($C_{16}$-$C_{24}$) ether,
the amount of the (a) first anionic surfactant(s) in the composition ranges from 0.1 to 3% by weight, relative to the total weight of the composition,
the amount of the (b) second anionic surfactant(s) in the composition ranges from 0.02 to 3% by weight, relative to the total weight of the composition,
the amount of the (c) nonionic surfactant(s) in the composition ranges from 0.1 to 5% by weight, relative to the total weight of the composition, and
the amount of the (d) thickener(s) in the composition ranges from 0.01 to 5% by weight, relative to the total weight of the composition.

2. The composition according to claim 1, wherein the (b) second anionic surfactant is selected from cocoyl or lauroyl alanines and salts thereof.

3. The composition according to claim 1, wherein the (b) second anionic surfactant is selected from cocoyl or lauroyl glycines and salts thereof.

4. The composition according to claim 1, wherein the composition further comprises water.

5. The composition according to claim 1, wherein the composition further comprises at least one fatty acid.

6. The composition according to claim 1, wherein the composition is a cosmetic composition.

7. A cosmetic process for treating a keratin substance, comprising: applying the composition according to claim 1 to the keratin substance.

* * * * *